United States Patent [19]
Kirby et al.

[11] Patent Number: 5,336,667
[45] Date of Patent: Aug. 9, 1994

[54] METHOD FOR INHIBITING THE AHESION OF PLATELET WITH ALBOAGGREGINS: PLATELET AGONISTS WHICH BIND TO PLATELET MEMBRANE GLYCOPROTEIN IB

[75] Inventors: Edward P. Kirby, Philadelphia; Man-ling Peng, Bensalem, both of Pa.

[73] Assignee: Temple University of the Commonwealth System of Higher Education, Philadelphia, Pa.

[21] Appl. No.: 893,929

[22] Filed: Jun. 5, 1992

Related U.S. Application Data

[63] Continuation-in-part of Ser. No. 803,630, Dec. 3, 1991, abandoned.

[51] Int. Cl.$^5$ .................. A61K 37/00; A01N 37/18; C07H 17/00; C07K 3/00
[52] U.S. Cl. .......................... 514/12; 514/2; 514/8; 530/350; 536/23.5; 435/6
[58] Field of Search ............... 530/350, 351, 387, 388, 530/412; 536/23.5; 435/6, 7; 514/2, 8, 12

[56] References Cited
PUBLICATIONS

Andrews et al., Biochemistry, 28, 8317–8326 (1989).
Read et al., Blood 73, No. 3, 1031–1035 (Aug. 15, 1989).
Sanders et al., Laboratory Investig. 89, 443–452 (1988).
Scarborough et al., Blood 78, p. 394a, Supp. I, Abs. #1568 (Nov. 15, 1991).
Peng et al., FASEB Journal 4, A1788, Abs. #555 (Apr. 16, 1990).
Peng et al., FASEB Journal 5, A522, Abs. #878 (Mar. 11, 1991).
Peng et al., Thromb. Haemostas, 65(6), 918, Abs. #918 (Jun. 5, 1991).
Peng et al., Biochemistry 30, 11524–11536 (Dec. 10, 1991).

Primary Examiner—Robert J. Hill, Jr.
Assistant Examiner—Gian P. Wang
Attorney, Agent, or Firm—Seidel, Gonda, Lavorgna & Monaco

[57] ABSTRACT

A family of proteins are provided which may be purified from snake venom. Each protein binds to the 45 kDa N-terminal domain of human platelet glycoprotein Ib, thereby inhibiting the binding of Von Willebrand factor to the domain. The proteins exist as multimers of individual polypeptide chains. The single polypeptide chains are useful for inhibiting the adhesion of platelets to subendothelial components of blood vessel walls exposed as the result of vascular damage.

32 Claims, 8 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 131 amino acids
( B ) TYPE: amino acid
( C ) TOPOLOGY: linear ( x i ) SEQUENCE DESCRIPTION: SEQ ID NO:1:

```
Asp Cys Pro Ser Asp Trp Ser Ser Tyr Asp Gln Tyr Cys Tyr Arg
                5                    10                  15

Val Phe Lys Arg Leu Gln Thr Trp Glu Asp Ala Glu Arg Phe Cys
                20                   25                  30

Ser Glu Gln Ala Asn Asp Gly His Leu Val Ser Ile Glu Ser Ala
                35                   40                  45

Gly Glu Ala Asp Phe Val Thr Gln Leu Val Ser Glu Asn Ile Arg
                50                   55                  60

Ser Glu Lys His Tyr Val Trp Ile Gly Leu Arg Val Gln Gly Lys
                65                   70                  75

Gly Gln Gln Cys Ser Ser Glu Trp Ser Asp Gly Ser Ser Val His
                80                   85                  90
```

```
Tyr  Asp  Asn  Leu  Gln  Glu  Lys  Asn  Thr  Arg  Lys  Cys  Tyr  Gly  Leu
              95                      100                          105

Glu  Lys  Arg  Ala  Glu  Phe  Arg  Thr  Trp  Ser  Asn  Val  Tyr  Cys  Gly
              110                     115                          120

His  Glu  Tyr  Pro  Phe  Val  Cys  Lys  Phe  Xaa  Arg
              125                     130
```

( 2 ) INFORMATION FOR SEQ ID NO:2:

( i ) SEQUENCE CHARACTERISTICS:
        ( A ) LENGTH: 134 amino acids
        ( B ) TYPE: amino acid
        ( C ) TOPOLOGY: linear ( x i ) SEQUENCE DESCRIPTION: SEQ ID NO:2:

```
Asp  Phe  His  Cys  Leu  Pro  Gly  Trp  Ser  Ala  Tyr  Asp  Gln  Tyr  Cys
              5                       10                           15

Tyr  Arg  Val  Phe  Asn  Glu  Pro  Lys  Asn  Trp  Glu  Asp  Ala  Glu  Arg
              20                      25                           30

Phe  Cys  Ala  Lys  Gln  Ala  Asp  Ser  Gly  His  Leu  Val  Ser  Ile  Glu
              35                      40                           45

Thr  Met  Gly  Glu  Ala  Asp  Phe  Val  Ala  Gln  Leu  Ile  Ser  Glu  Asn
              50                      55                           60

Ile  Gln  Ser  Lys  Glu  His  Tyr  Val  Trp  Ile  Gly  Leu  Lys  Val  Gln
              65                      70                           75

Asn  Lys  Glu  Gln  Gln  Cys  Ser  Ser  Glu  Trp  Ser  Asp  Gly  Ser  Ser
              80                      85                           90

Val  Thr  Tyr  Glu  Asn  Leu  Ile  Lys  Leu  Tyr  Met  Arg  Lys  Cys  Gly
              95                      100                          105

Ala  Leu  Glu  Gln  Glu  Ser  Gly  Phe  Arg  Lys  Trp  Ile  Asn  Leu  Gly
              110                     115                          120

Cys  Ile  Gln  Leu  Asn  Pro  Phe  Val  Cys  Lys  Phe  Pro  Pro  Gln
              125                     130
```

( 2 ) INFORMATION FOR SEQ ID NO:3:

( i ) SEQUENCE CHARACTERISTICS:
        ( A ) LENGTH: 125 amino acids
        ( B ) TYPE: amino acid
        ( C ) TOPOLOGY: linear ( x i ) SEQUENCE DESCRIPTION: SEQ ID NO:3:

```
Gly  Phe  Cys  Cys  Pro  Phe  Gly  Trp  Ser  Ser  Tyr  Glu  Gly  Tyr  Cys
              5                       10                           15

Tyr  Lys  Val  Tyr  Asn  Lys  Lys  Met  Asn  Trp  Glu  Asp  Ala  Glu  Ser
              20                      25                           30

Phe  Cys  Arg  Glu  Gln  His  Lys  Arg  Ser  His  Leu  Val  Ser  Phe  His
              35                      40                           45

Ser  Ser  Gly  Glu  Val  Asp  Phe  Val  Val  Ser  Lys  Thr  Phe  Pro  Ile
              50                      55                           60

Leu  Arg  Tyr  Asp  Phe  Val  Trp  Met  Gly  Leu  Ser  Asp  Ile  Trp  Lys
              65                      70                           75

Glu  Cys  Thr  Lys  Glu  Trp  Ser  Asp  Gly  Ala  Arg  Leu  Asp  Tyr  Lys
              80                      85                           90

Ala  Trp  Ser  Gly  Lys  Ser  Tyr  Cys  Leu  Val  Ser  Lys  Thr  Thr  Asn
              95                      100                          105

Asn  Glu  Trp  Leu  Ser  Met  Asp  Cys  Ser  Arg  Thr  Leu  Tyr  Pro  Val
              110                     115                          120

Cys  Lys  Phe  Xaa  Gly
              125
```

( 2 ) INFORMATION FOR SEQ ID NO:4:

( i ) SEQUENCE CHARACTERISTICS:
        ( A ) LENGTH: 123 amino acids
        ( B ) TYPE: amino acid
        ( C ) TOPOLOGY: linear ( x i ) SEQUENCE DESCRIPTION: SEQ ID NO:4:

```
Asp Cys Pro Ser Asp Trp Ser Ser Tyr Glu Gly His Cys Tyr Arg
                 5                  10                  15

Val Phe Asn Glu Pro Gln Asn Trp Ala Asp Ala Glu Lys Phe Cys
                20                  25                  30

Thr Gln Gln His Lys Gly Ser His Leu Val Ser Phe Gln Ser Ser
                35                  40                  45

Glu Glu Ala Asp Phe Val Val Gln Met Thr Arg Pro Ile Leu Asn
                50                  55                  60

Ala Asn Leu Val Trp Ile Gly Leu Ser Asn Leu Trp Asn Gly Cys
                65                  70                  75

Asn Ser Gln Trp Ser Asp Gly Thr Xaa Leu Asp Tyr Lys Xaa Trp
                80                  85                  90

Arg Glu Gln Phe Glu Cys Leu Val Ser Arg Thr Thr Asn Asn Glu
                95                 100                 105

Trp Leu Ser Met Asp Cys Ser Ser Thr His Ser Phe Val Cys Glu
               110                 115                 120

Phe Gln Ala
```

( 2 ) INFORMATION FOR SEQ ID NO:5:

( i ) SEQUENCE CHARACTERISTICS:
        ( A ) LENGTH: 132 amino acids
        ( B ) TYPE: amino acid
        ( C ) TOPOLOGY: linear ( x i ) SEQUENCE DESCRIPTION: SEQ ID NO: 5:

```
Asp Cys Pro Ser Asp Trp Ser Ser Phe Lys Gln Tyr Cys Tyr Gln
                 5                  10                  15

Ile Val Lys Glu Leu Lys Thr Trp Glu Asp Ala Glu Lys Phe Cys
                20                  25                  30

Ser Glu Gln Ala Asn Asp Gly His Leu Val Ser Ile Glu Ser Tyr
                35                  40                  45

Arg Glu Ala Val Phe Val Ala Glu Leu Leu Ser Glu Asn Val Lys
                50                  55                  60

Thr Thr Lys Tyr Asn Val Trp Ile Gly Leu Ser Val Gln Asn Lys
                65                  70                  75

Glu Gln Gln Cys Ser Ser Glu Trp Ser Asp Gly Ser Ser Val Xaa
                80                  85                  90

Tyr Glu Asn Leu Ile Lys Pro Asn Pro Lys Lys Cys Phe Val Leu
                95                 100                 105

Lys Lys Glu Ser Glu Phe Arg Thr Trp Ser Asn Val Tyr Cys Glu
               110                 115                 120

Gln Lys His Ile Phe Met Cys Lys Phe Leu Gly Ser
               125                 130
```

( 2 ) INFORMATION FOR SEQ ID NO:6:

( i ) SEQUENCE CHARACTERISTICS:
        ( A ) LENGTH: 107 amino acids
        ( B ) TYPE: amino acid
        ( C ) TOPOLOGY: linear ( x i ) SEQUENCE DESCRIPTION: SEQ ID NO: 6:

```
Asp  Cys  Pro  Ser  Asp  Trp  Ser  Ser  Tyr  Asp  Leu  Tyr  Cys  Tyr  Lys
                    5                        10                         15

Val  Phe  Gln  Gln  Arg  Met  Asn  Trp  Glu  Asp  Ala  Glu  Gln  Phe  Cys
                    20                       25                        30

Arg  Gln  Gln  His  Thr  Gly  Ser  His  Leu  Leu  Ser  Phe  His  Ser  Ser
                    35                       40                        45

Glu  Lys  Ala  Asp  Phe  Val  Trp  Ile  Gly  Leu  Thr  Asp  Val  Trp  Ser
                    50                       55                        60

Ala  Cys  Arg  Leu  Gln  Trp  Ser  Asp  Gly  Thr  Glu  Leu  Lys  Tyr  Asn
                    65                       70                        75

Ala  Trp  Thr  Ala  Glu  Ser  Glu  Cys  Ile  Ala  Ser  Lys  Thr  Thr  Asp
                    80                       85                        90

Asn  Gln  Trp  Trp  Thr  Arg  Ser  Cys  Ser  Lys  Thr  Tyr  Pro  Phe  Val
                    95                       100                       105

Cys  Lys
```

( 2 ) INFORMATION FOR SEQ ID NO:7:

( i ) SEQUENCE CHARACTERISTICS:
( A ) LENGTH: 130 amino acids
( B ) TYPE: amino acid
( C ) TOPOLOGY: linear ( x i ) SEQUENCE DESCRIPTION: SEQ ID NO:7:

```
Asp  Cys  Pro  Ser  Asp  Trp  Ser  Ser  Phe  Lys  Gln  Tyr  Cys  Tyr  Gln
                    5                        10                        15

Ile  Val  Lys  Glu  Leu  Lys  Thr  Trp  Glu  Asp  Ala  Glu  Arg  Phe  Cys
                    20                       25                        30

Ser  Glu  Gln  Ala  Asn  Asp  Gly  His  Leu  Val  Ser  Ile  Glu  Ser  Tyr
                    35                       40                        45

Arg  Glu  Ala  Val  Phe  Val  Ala  Glu  Leu  Leu  Ser  Glu  Asn  Val  Lys
                    50                       55                        60

Lys  Tyr  His  Val  Trp  Ile  Gly  Leu  Ser  Val  Gln  Asn  Lys  Gly  Gln
                    65                       70                        75

Gln  Cys  Ser  Ser  Glu  Trp  Ser  Asp  Gly  Ser  Ser  Val  Ser  Tyr  Glu
                    80                       85                        90

Asn  Leu  Val  Lys  Pro  Asn  Pro  Lys  Lys  Cys  Phe  Val  Leu  Lys  Lys
                    95                       100                       105

Glu  Ser  Glu  Phe  Lys  Thr  Trp  Ser  Asn  Val  Tyr  Cys  Glu  Gln  Lys
                    110                      115                       120

His  Ile  Phe  Met  Cys  Lys  Phe  Leu  Gly  Ser
                    125                      130
```

( 2 ) INFORMATION FOR SEQ ID NO:8:

( i ) SEQUENCE CHARACTERISTICS:
( A ) LENGTH: 128 amino acids
( B ) TYPE: amino acid
( C ) TOPOLOGY: linear ( x i ) SEQUENCE DESCRIPTION: SEQ ID NO:8:

```
Asp  Cys  Pro  Ser  Asp  Trp  Ser  Ser  Tyr  Asp  Leu  Tyr  Cys  Tyr  Lys
                    5                        10                        15

Val  Phe  Gln  Glu  Arg  Met  Asn  Trp  Glu  Asp  Ala  Glu  Gln  Phe  Cys
                    20                       25                        30

Arg  Gln  Gln  His  Thr  Gly  Xaa  Xaa  Xaa  Xaa  Xaa  Xaa  His  Ser  Ser
                    35                       40                        45

Glu  Glu  Val  Asp  Phe  Val  Xaa  Xaa  Xaa  Xaa  Xaa  Xaa  Xaa  Xaa  Xaa
```

|  | | | | | 50 | | | | | 55 | | | | | 60 |
|---|---|---|---|---|---|---|---|---|---|---|---|---|---|---|---|
| Xaa | Xaa | Xaa | Xaa | Xaa | Xaa | Xaa | Trp | Ile | Gly | Leu | Thr | Asp | Val | Xaa |
| | | | | | 65 | | | | | 70 | | | | | 75 |
| Xaa | Trp | Ser | Ala | Cys | Arg | Leu | Gln | Trp | Ser | Asp | Gly | Thr | Glu | Leu |
| | | | | | 80 | | | | | 85 | | | | | 90 |
| Xaa | Lys | Tyr | Asn | Ala | Trp | Thr | Ala | Glu | Ser | Glu | Cys | Ile | Ala | Ser |
| | | | | | 95 | | | | | 100 | | | | | 105 |
| Xaa | Xaa | Xaa | Xaa | Xaa | Xaa | Xaa | Xaa | Trp | Thr | Arg | Ser | Cys | Ser |
| | | | | | 110 | | | | | 115 | | | | | 120 |
| Arg | Thr | Tyr | Pro | Phe | Val | Cys | Lys |
| | | | | | 125 |

(2) INFORMATION FOR SEQ ID NO:9:

(i) SEQUENCE CHARACTERISTICS:
        (A) LENGTH: 133 amino acids
        (B) TYPE: amino acid
        (C) TOPOLOGY: linear (xi) SEQUENCE DESCRIPTION: SEQ ID NO:9:

| Asp | Gln | Asp | Cys | Leu | Ser | Gly | Trp | Ser | Phe | Tyr | Glu | Gly | His | Cys |
|---|---|---|---|---|---|---|---|---|---|---|---|---|---|---|
| | | | | 5 | | | | | 10 | | | | | 15 |
| Tyr | Gln | Leu | Phe | Arg | Leu | Lys | Thr | Trp | Asp | Glu | Ala | Glu | Lys | Tyr |
| | | | | 20 | | | | | 25 | | | | | 30 |
| Cys | Asn | Gln | Trp | Asp | Gly | Gly | His | Leu | Val | Ser | Ile | Glu | Ser | Asn |
| | | | | 35 | | | | | 40 | | | | | 45 |
| Ala | Lys | Ala | Glu | Phe | Val | Ala | Gln | Leu | Ile | Ser | Arg | Lys | Leu | Pro |
| | | | | 50 | | | | | 55 | | | | | 60 |
| Lys | Ser | Ala | Ile | Glu | Asp | Arg | Val | Trp | Ile | Gly | Leu | Arg | Asp | Arg |
| | | | | 65 | | | | | 70 | | | | | 75 |
| Ser | Lys | Arg | Glu | Gln | Cys | Gly | His | Leu | Trp | Thr | Asp | Asn | Ser | Phe |
| | | | | 80 | | | | | 85 | | | | | 90 |
| Val | His | Tyr | Glu | His | Val | Val | Pro | Pro | Thr | Lys | Cys | Phe | Val | Leu |
| | | | | 95 | | | | | 100 | | | | | 105 |
| Glu | Arg | Gln | Thr | Glu | Phe | Arg | Lys | Trp | Ile | Ala | Val | Asn | Cys | Glu |
| | | | | 110 | | | | | 115 | | | | | 120 |
| Phe | Lys | Phe | Pro | Phe | Val | Cys | Lys | Ala | Lys | Ile | Pro | Arg |
| | | | | 125 | | | | | 130 |

(2) INFORMATION FOR SEQ ID NO:10:

(i) SEQUENCE CHARACTERISTICS:
        (A) LENGTH: 123 amino acids
        (B) TYPE: amino acid
        (C) TOPOLOGY: linear (xi) SEQUENCE DESCRIPTION: SEQ ID NO:10:

| Asn | Cys | Leu | Pro | Asp | Trp | Ser | Val | Tyr | Glu | Gly | Tyr | Cys | Tyr | Lys |
|---|---|---|---|---|---|---|---|---|---|---|---|---|---|---|
| | | | | 5 | | | | | 10 | | | | | 15 |
| Val | Phe | Lys | Glu | Arg | Met | Asn | Trp | Ala | Asp | Ala | Glu | Lys | Phe | Cys |
| | | | | 20 | | | | | 25 | | | | | 30 |
| Met | Lys | Gln | Val | Lys | Asp | Gly | His | Leu | Val | Ser | Phe | Arg | Asn | Ser |
| | | | | 35 | | | | | 40 | | | | | 45 |
| Lys | Xaa | Xaa | Xaa | Xaa | Xaa | Xaa | Xaa | Xaa | Xaa | Xaa | Xaa | Xaa |
| | | | | 50 | | | | | 55 | | | | | 60 |
| Xaa | Xaa | Lys | Met | Glu | Leu | Val | Trp | Ile | Gly | Leu | Ser | Asp | Tyr | Trp |
| | | | | 65 | | | | | 70 | | | | | 75 |
| Arg | Asp | Cys | Tyr | Trp | Glu | Trp | Ser | Asp | Gly | Ala | Gln | Leu | Asp | Tyr |
| | | | | 80 | | | | | 85 | | | | | 90 |

```
Lys  Ala  Trp  Asp  Asn  Glu  Arg  His  Cys  Phe  Ala  Ala  Lys  Thr  Thr
                    95                      100                     105

Asp  Asn  Gln  Trp  Met  Arg  Arg  Lys  Cys  Ser  Gly  Glu  Phe  Tyr  Phe
                    110                     115                     120

Val  Cys  Lys
```

METHOD FOR INHIBITING THE AHESION OF PLATELET WITH ALBOAGGREGINS: PLATELET AGONISTS WHICH BIND TO PLATELET MEMBRANE GLYCOPROTEIN IB

REFERENCE TO GOVERNMENT GRANT

The invention described herein was supported in part by National Institutes of Health grant HL 27993. The government has certain rights in the invention.

CROSS REFERENCE TO RELATED APPLICATION

This is a continuation-in-part of our application Ser. No. 803,630, filed Dec. 3, 1991 now abandoned.

FIELD OF THE INVENTION

The invention relates to novel polypeptides which specifically bind to human platelet membrane glycoprotein Ib.

BACKGROUND OF THE INVENTION

When blood vessels are damaged, yon Willebrand factor (vWF) is needed for platelets to recognize the damaged vascular endothelium and to form aggregates upon it. Human vWF circulates in plasma as a series of disulfide-linked multimers ranging in molecular weight from 350,000 to $1 \times 6$ (Girma et al., Blood 70:605 (1987)). Platelet adhesion to subendothelial components exposed by vascular damage is the first step in the platelet's response to such damage. Adhesion involves the binding of vWF to the subendothelium, and subsequent binding of platelets to vWF via a specific receptor on the platelet surface associated with platelet membrane glycoprotein Ib (GPIb). The latter is one of the major platelet membrane glycoproteins. There are approximately 25,000 copies of GPIb per platelet. GPIb contains two disulfide-linked subunits, GPIbα (Mr=145 kDa) and GPIbβ (Mr=24 kDa). Both chains appear to be integral membrane glycoproteins containing hydrophobic transmembrane domains (Clemetson et al., Proc. Natl. Acad. Sci. USA 78:2712 (1981)). The subunits are complexed with glycoprotein IX (Mr=22 kDa). Antibodies to vWF and GPIb can inhibit the adhesion response.

The exposed subendothelium is a matrix composed of collagen and elastin fibers, glycosaminoglycans, fibronectin, vWF, and other proteins. The yon Willebrand factor appears to be essential to the process by which flowing blood platelets recognize and adhere to areas of damaged endothelium. Individuals afflicted with yon Willebrand's disease, who have defective or deficient vWF, have a bleeding syndrome due to ineffective platelet-mediated hemostasis (Zimmerman and Ruggeri, Prog. Hemost. Thromb. 6, 203–236 (1982)).

Platelet adhesion to exposed endothelial components stimulates platelet secondary responses associated with shape change, thromboxane production, release of granular constituents, and exposure of other receptors on the platelet surface, such as the receptors associated with glycoprotein IIb/IIIa. These responses promote the formation of platelet aggregates and fibrin deposition at the site of injury.

Snake venom is a rich source of reagents functioning as either agonists or antagonists of the formation of platelet hemostatic plugs. Numerous platelet agonists isolated from snake venoms are known. Teng et al., Biochim. Biophys. Acta 757, 332–341 (1984) reported a protease, isolated from *Vipera russellii* venom, which possesses procoagulant activity. It activates Factor X in the presence of calcium and leads to platelet aggregation in platelet-rich plasma.

Thrombocytin, a thrombin-like enzyme from *Bothrops atrox* venom (Niewiarowski et al., Biochemistry 18, 3570–3577 (1979)), and crotalocytin, from *Crotalus horridus horridus* venom (Schmaier & Colman, Blood 56(6), 1020–1028, (1980)) aggregate platelets directly, probably by a mechanism similar to thrombin.

Disintegrins represent a new class of low molecular weight, RGD-containing peptides from the venoms of various snakes. They are platelet GPIIb/IIIa antagonists and potent inhibitors of platelet aggregation and fibrinogen binding to platelets. (Dennis et al., Proc. Natl. Acad. Sci. USA 87:2471 (1989); Gould et al., P.S.E.B.M. 195:168 (1990)). The disintegrin trigramin, a naturally occurring peptide purified from *Trimeresurus gramineus* venom, blocks the binding of fibrinogen and human vWF to the glycoprotein IIb/IIIa complex in thrombin-activated platelets (Huang et al., Biochemistry 28, 661–666 (1989)) but does not affect binding of vWF to GPIb. The motifs of disintegrin as well as metalloproteinase are present in hemorrhagic factors (isolated from *T. flavoviridis* venom) which are potent platelet antagonists (Takeya et al., J. Biol. Chem. 265:16068 (1990)). Albolabrin, isolated from *Trimeresurus albolabris* venom (Williams et al., Biochim. Biophys. Acta. 1039, 81–89 (1990)), showed a similar inhibitory activity in platelet aggregation. The biological activities of trigramin and albolabrin appear to depend upon the presence of an RGD sequence.

The effect of twenty Australian snake venoms (nineteen elapid and one hydrophid) and four crotalid venoms on human fresh and fixed platelets has been examined by Marshall & Herrmann, Thrombosis Research 54, 269–275 (1989). All venoms, except the hydrophid venom, which requires the presence of a plasma co-factor, directly caused fresh platelets to aggregate irreversibly.

Five snake venom lectins have been reported by Ogilvie et al., Thromb. Haem. 62, 704–707 (1989), which agglutinate red cells and stimulate the aggregation of human platelets. The lectin-induced platelet aggregation has been inhibited by a monoclonal antibody to GPIIb/IIIa (Ogilvie et al., Thromb. Haem. 62:704 (1989)).

Botrocetin, purified from the venom of the South American pit viper, has previously been shown to cause vWF-dependent agglutination of platelets (Andrews et al., Biochemistry 28, 8317–8326 (1989) ) . Botrocetin induces platelet agglutination by facilitating binding of vWF to GPIb, although botrocetin alone does not stimulate platelet agglutination directly (Sanders, et al., Lab. Invest. 59, 443–452 (1988)). Both vWF and a 52/48-kDa dimeric fragment of vWF bound specifically and saturably to botrocetin-coupled beads. However, glycocalicin, a proteolytic fragment of the α-chain of GPIb that contains the vWF-binding domain, did not bind to immobilized botrocetin (Id.). This agrees with the observation by Read et al., Blood 74(3) 1031–1035 (1989) that botrocetin appears to act in a two-step manner, first binding with vWF to form a complex, which then binds to GPIb to cause agglutination.

Ristocetin is an antibiotic isolated from *Nocardia lurida* that can cause platelet agglutination in the presence of human vWF. (Howard & Firkin, Thromb.

*Diath. Haemorrh.*, 26, 362–369 (1971)). It has been widely used as a cofactor to induce human vWF binding to platelet GPIb. Unlike botrocetin, it is not clear whether ristocetin promotes the binding of vWF to platelet GPIb by interacting with the vWF molecule or with its receptor on GPIb. Id.

Binding of human vWF to platelets in vitro occurs in the presence of ristocetin or botrocetin, whereas bovine vWF directly induces platelet agglutination. (Kirby, R. *J. Lab. Clin. Med.* 100:963 (1982). Bovine and human vWF bind to the same region on platelet GPIb. (Suzuki et al., *Thromb. Res.* 17:215 (1980)).

While the foregoing molecules are active in binding platelets and/or inducing their agglutination, they do so by a mechanism distinct from that of the hereinafter described novel polypeptides which bind GPIb close to or at the platelet binding site for vWF.

SUMMARY OF THE INVENTION

A family of substantially purified platelet-aggregating proteins obtainable from snake venom is provided. Each such protein comprises two or more cystine-crosslinked polypeptide chains. Each chain has a molecular weight of from about 10 to about 20 kDa. The protein, and the isolated polypeptide chains, bind to the about 45 kDa N-terminal domain of human platelet glycoprotein Ib, thereby inhibiting the binding of Von Willebrand factor to the domain. The platelet-binding activity of the protein is inhibited by monoclonal antibodies which specifically bind to the 45 kDa N-terminal domain of human platelet glycoprotein Ib. The protein furthermore fails to bind human platelets which are treated with proteolytic enzymes to remove the 45 kDa N-terminal domain from human platelet glycoprotein Ib. By "the about 45 kDa N-terminal domain of human platelet glyco-protein Ib" is meant the about 45 kDa N-terminal portion of the GPIb molecule liberated by cleavage of GPIb with the enzyme elastase.

One such protein, hereinafter identified as alboaggregin A (AL-A) may be obtained in substantially pure chemical form from *Trimeresurus albolabris* venom. It has a molecular weight of about 45 kDa according to sodium dodecyl sulfate polyacrylamide gel electrophoresis (SDS-PAGE) under nonreducing conditions.

Polyacrylamide gel electrophoresis under reducing conditions demonstrates that AL-A contains two types of polypeptide chains, with molecular weights of about 18 kDa and about 15 kDA, respectively. Reverse-phase high performance liquid chromatography and amino acid sequencing reveals that each of these two types of chains is actually composed of two subtypes which differ in their amino acid sequences. Thus, AL-A comprises four non-identical polypeptide chains which have respective amino acid sequences of SEQ ID NOS: 1, 2, 3 and 4. A possible variation of SEQ ID NO:3 has been found, characterized by Asp at position three in lieu of Cys.

Two other such proteins, hereinafter identified as alboaggregin B1 and B2 (collectively hereinafter "AL-B"), may be obtained in substantially pure chemical form from *Trimeresurus albolabris* venom. Each of AL-B1 and -B2 comprise an about 23 kDa protein formed by an about 17 kDa polypeptide chain crosslinked to an about 14 kDa polypeptide chain by one or more interchain disulfide bonds (molecular weights are by SDS-PAGE). Each of the two polypeptide chains of AL-B1 and -B2 show strong homology to two of the chains of AL-A. AL-B1 and --B2 each comprise two non-identical polypeptide chains. The polypeptide chains of AL-B1 have amino acid sequences of SEQ ID NO:5 and SEQ ID NO:6. The two polypeptide chains of AL-B2 have amino acid sequences of SEQ ID NO:7 and SEQ ID NO:8.

Yet another protein, hereinafter identified as alboaggregin C (AL-C) is obtained in substantially pure chemical form from *Trimeresurus albolabris* venom as an about 100 kDa protein which likely comprises a hexamer composed of two types of chains. One chain type has a molecular weight of about 20 kDa. (Molecular weights are by SDS-PAGE). The other chain type has a weight of about 16 kDa. The individual polypeptide chains are held together by interchain disulfide bonds.

Another alboaggregin-like protein, hereinafter referred to as echicetin, is obtained in substantially pure chemical form from *Echis carinatus* venom, as an about 26 kDa protein which likely comprises a dimer composed of two types of chains. One chain type has a molecular weight of about 15 kDa and the other has a molecular weight of about 13 kDa. The individual polypeptide chains are held together by one or more interchain disulfide bonds. The two non-identical polypeptide chains of echicetin have respective amino acid sequences of SEQ ID NO:9 and SEQ ID NO:10.

Described herein is the purification of echicetin from *E. carinatus* venom which specifically inhibits the binding of alboaggregin and vWF to platelet GPIb without inducing platelet agglutination. Echicetin may be isolated by reverse phase and ion exchange chromatography. It specifically inhibits fixed platelet agglutination induced by several platelet glycoprotein Ib (GPIb) agonists (such as human von Willebrand Factor (vWF) in the presence of botrocetin, bovine vWF and alboaggregins).

Echicetin is a heterodimer with two subunits. Its stability is remarkable in that its activity survives exposure to 0.1% trifluoroacetic acid in 51% acetonitrile, as well as reduction and alkylation. Echicetin binds poorly to Mono-Q, a strong anion exchange resin used for purifying alboaggregins, but binds well to Mono-S, a strong cation exchange resin. This suggests that echicetin and the alboaggregins may differ significantly in their content of charged amino acids. Both echicetin and AL-B eluted from $C_{18}$ reverse-phase columns at similar acetonitrile concentrations, indicating that they have similar hydrophobic characteristics.

While echicetin has been isolated from *E. carinatus*, rather than *T. albolabris*, it is included in the class of "algoaggregin" proteins by virtue of numerous characteristics shared with AL-A, AL-B and AL-C. In contrast to alboaggregins, native echicetin binds to GPIb but does not induce platelet agglutination.

Like the alboaggregins, echicetin strongly inhibits vWF binding to platelet GPIb. The binding of echicetin is blocked by monoclonal antibody against the 45 kDa N-terminal domain of GPIb but not by antibodies to other regions. The binding domain for echicetin on platelet GPIb is thus located on the 45 kDa domain at a site close to or identical with the binding sites for AL-B and vWF.

Binding of $^{125}$I-bovine vWF to fixed platelets is strongly inhibited by echicetin. Conversely, bovine vWF is only a much weaker inhibitor of $^{125}$I-echicetin binding to platelets. Echicetin selectively binds to platelets but not to erythrocytes and neutrophils.

As described in more detail hereinafter, we have demonstrated that echicetin significantly prolongs bleeding time in vivo. Echicetin and the alboaggregins in general, bind to GPIb, thereby blocking vWF-induced primary platelet adhesion to the subendothelium.

The invention also relates to analogs of the native polypeptides described herein. By "analog" with respect to an alboaggregin or alboaggregin-like polypeptide is meant a modified polypeptide having an amino acid sequence substantially the same as that of the naturally occurring molecule in which one or more amino acids have been deleted or substituted, or in which one or more amino acids have been inserted; which modified polypeptide retains the property of binding to the about 45 kDa N-terminal domain of human platelet glycoprotein Ib to inhibit the binding of von Willebrand factor to said domain.

The individual polypeptide chains comprising the native alboaggregin proteins have therapeutic utility. Thus, the invention provides a platelet-binding, single-chain polypeptide obtainable by partial reduction of a multi-chain native snake venom protein, which single chain polypeptide has a molecular weight of from about 10 kDa to about 20 kDa. The single-chain polypeptide binds to the about 45 kDa N-terminal domain of human platelet glycoprotein Ib to inhibit the binding of vWF to that domain, without inducing substantial platelet aggregation. Antithrombotic compositions comprise one or more of the single-chain polypeptides in combination with a pharmaceutically acceptable carrier are also provided.

The invention further provides a method for inhibiting the adhesion of platelets to exposed subendothelial components of blood vessel walls. Platelets are treated with one or more of the aforesaid platelet-binding, single-chain polypeptides. In another embodiment, an effective amount of the single-chain polypeptide is administered to a mammal in need of treatment for inhibition of platelet adhesion to exposed subendothelial components.

The invention further provides a process for isolating the alboaggregins from the venom of a snake by
(a) dissolving lyophilized snake venom in a solvent;
(b) fractionating the venom to separate the proteins contained therein;
(c) assaying the fractions for the ability to agglutinate fixed platelets and/or inhibit the agglutination of fixed platelets by vWF; and
(d) purifying from the platelet-agglutinating fractions a protein which inhibits the binding of von Willebrand factor to fixed platelets.

Partial reduction of the interchain disulfide bonds of the purified protein generates single-chain polypeptides. The free sulfhydryl groups of the single-chain polypeptides may be blocked with a blocking agent to prevent disulfide bond reformation.

GPIb is found only on platelets, megakaryocytes (the cellular precursors of platelets) and endothelial cells. A method is therefore provided for identifying platelets, megakaryocytes or endothelial cells in the presence of other cell types, comprising contacting a specimen with detectably-labeled alboaggregin or detectably-labelled subunit thereof, and assaying said sample for cell-binding by the labelled alboaggregin or subunit. By "subunit" is meant an individual polypeptide chain of an alboaggregin, or any combination of such individual polypeptide chains.

The invention further provides a method for detecting functional platelet GPIb in platelet specimens. A platelet specimen is contacted with alboaggregin, and the extent of platelet aggregation is determined. Since alboaggregin-induced platelet aggregation requires intact GPIb on platelets, the presence or absence of aggregation indicates the presence or absence of intact GPIb on the platelets under study.

In a related invention, a platelet specimen is contacted with detectably-labelled alboaggregin or detectably-labelled subunit thereof, and the platelet specimen is assayed for binding of the labelled alboaggregin or subunit. The presence or absence of binding indicates the presence or absence of intact GPIb on the platelets under study.

The invention may also be practiced by expression of the corresponding nucleic acid sequences of the peptides in heterologous host systems for production of the disclosed biosynthetic antithrombotic proteins and variations thereof.

DETAILED DESCRIPTION OF THE INVENTION

I. Introduction

Figure 1:
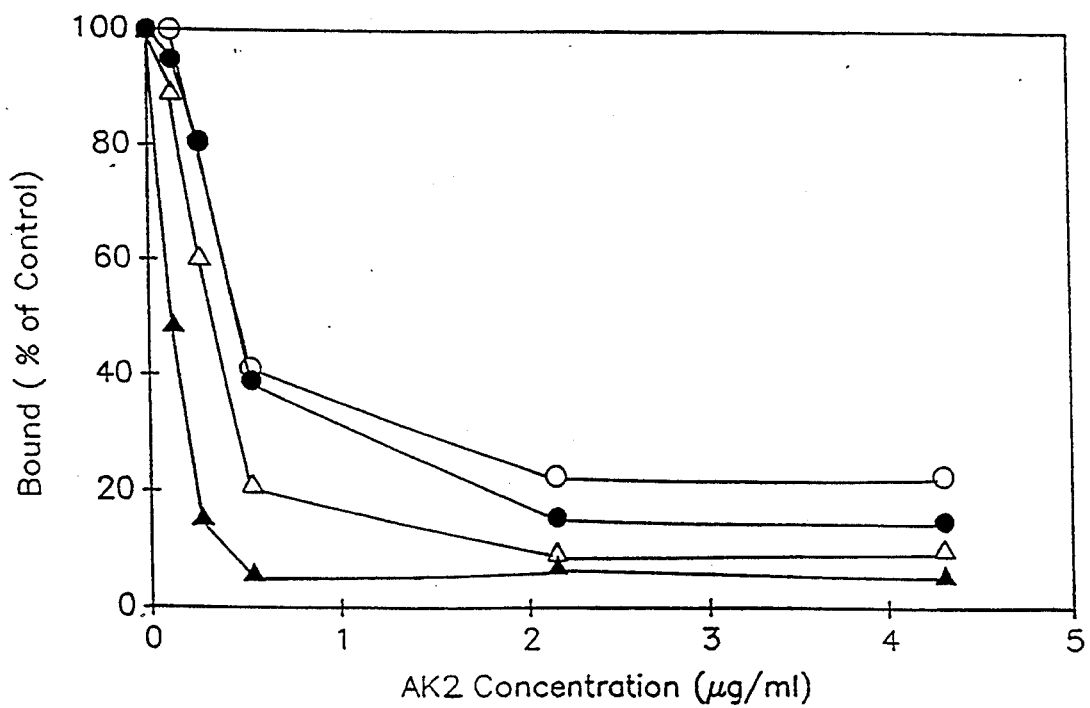
FIG. 1 is a plot of the inhibitory effect on $^{125}$I-alboaggregins and $^{125}$I-bovine vWF binding to platelets exerted by monoclonal antibody (AK2) specific for the 45 kDa N-terminal fragment of GP Ib: AL-A (○—○); AL-B (●—●); AL-C (△—△); bovine vWF (▲—▲).

The alboaggregins are a class of novel polypeptides which act as platelet adhesion inhibiting agents. They bind to platelets at or near the vWF binding site in the N-terminal region of GPIb, thereby competitively inhibiting platelet binding of vWF. This results in the specific inhibition of the vWF-mediated platelet response, leaving other platelet responses intact.

The native alboaggregins exist as multimers (dimers, tetramers, hexamers, etc.) of, for the most part, non-identical polypeptide chains. The multimeric construction of the alboaggregins accounts for their platelet aggregating activity. The individual polypeptide chains are cysteine-crosslinked to one another, that is, the chains are held together by interchain disulfide bonds. Partial reduction of the intact native molecule, and cleavage of the interchain disulfide bonds, can abolish this agglutinating activity. The result is a therapeutic polypeptide which may be effectively utilized to inhibit binding of platelets to vWF on the subendothelium exposed by damage to the vascular wall.

In addition to partial reduction of intact multimeric proteins, therapeutically useful agents may be developed from the alboaggregins by proteolysis of the native molecule, amino acid modification or substitution Via recombinant DNA technology, which may preferentially inactivate one of the subunits, rendering the protein effectively monovalent. Alternatively, monovalent peptides analogous to the domains of the alboaggregins involved in platelet binding may be prepared by chemical peptide synthesis or recombinant DNA technology.

The alboaggregins may be prepared from the venom of a variety of snakes, by the separation and screening techniques hereinafter described. Several such suitable venoms, such as the venom of *Trimeresurus albolabris*, are commercially available in lyophilized form.

Generally, the lyophilized venom is first dissolved in a suitable solvent, such as 0.05 M Tris buffer, pH 8.0. The venom solution may be advantageously centrifuged and/or filtered to remove undissolved material. The venom is then fractionated in order to separate the component proteins. The preferred separation means is high performance liquid column chromatography, under conditions which will not denature protein. Ion exchange materials, such as Mono-Q (Pharmacia Fine Chemicals, Piscataway, NJ), are the preferred separation media because they give efficient resolution of components using buffers that do not interfere with subsequent assays for alboaggregin activity. Further purification beyond that afforded by a single HPLC fractionation may be achieved, if necessary, by subsequent ion exchange, hydrophobic, or gel filtration chromatography.

Identification of chromatographic fractions containing alboaggregin activity requires specific assays for alboaggregin activity in the presence of numerous other activities associated with the many other proteins found in snake venoms.

The primary assay for establishing the presence of alboaggregins in a chromatography fraction is the agglutination of fixed, washed human platelets. Agglutination is measured by the change in light transmittance in an aggregometer. The clumping of platelets is also observed macroscopically to ensure that the light transmittance changes observed are not due to volume changes in the platelets, or to platelet lysis. The platelets used should be fixed, such as by treatment with formalin or paraformaldehyde, to prevent artifacts caused by platelet responses subsequent to agglutination.

Once agglutination of fixed washed platelets by a protein fraction is established, one or more secondary assays may be employed to further confirm the presence of alboaggregins. According to one such assay, the platelet agglutination activity of the fraction is assayed in the presence of monoclonal antibodies specific for the 45 kDa N-terminal domain of GPIb, the site of alboaggregin binding, as hereinafter described. Such antibodies may be obtained by preparing the appropriate hybridomas, according to the conventional technique of Kohler and Milstein, originally reported in *Nature* 256, 493–497 (1975). The preparation of one such antibody specific for the 45 kDa N-terminal domain of GPIb, designated "APi", is described by Montgomery et al., *J. Clin. Inv.* 71 385–389 (1983). The same antibody is available from the Blood Research Institute of the Blood Center of Southeastern Wisconsin, Milwaukee, Wisconsin. The loss of platelet aggregating activity in the presence of AP1 is an indication that the aggregating agent present in the protein fraction under study is in fact an alboaggregin. Another monoclonal antibody specific for the 45 kDa N-terminal domain of GPIb, designated "AK2", is described by Berndt et al., *Biochemistry* 27, 663–640 (1988). The antibody was obtained from the Research Center for Thrombosis and Cardiovascular Disease, Department of Medicine, University of Sydney, Westmead, NSW, Australia.

The presence of alboaggregin in a fraction may also be confirmed by the loss of platelet agglutination activity following treatment of the platelets with an enzyme, such as elastase, which cleaves from platelet GPIb the 45 kDa fragment containing the alboaggregin binding site. Such an assay is described hereinafter.

Yet another assay to confirm the presence of alboaggregin in a fraction relies on the ability of alboaggregins to compete with vWF for binding to fixed platelets. The inhibition of platelet binding of suitably radiolabelled bovine vWF may thus be used as an indication that a protein isolated by chromatography is indeed an alboaggregin. Such competition assays are described hereinafter.

Prior to the screening of the isolated protein fraction for alboaggregin activity, the material should be substantially chemically purified by repeated chromatography, if necessary. Numerous contaminating activities have been observed in crude alboaggregin preparations, which may interfere with identification of alboaggregin activity. Crude preparations may contain lipases, which cause platelet lysis. Lysis can be detected by centrifugation or micro-scopic examination of the treated platelet suspensions. Proteolytic enzymes may also contaminate the preparation. Proteolytic enzymes may be detected with standard colorimetric or radioisotope assays for non-specific proteases. Thrombin-like enzymes, if present, can directly aggregate intact platelets in the absence of alboaggregin, or can induce platelet clumping if traces of fibrinogen remain in the suspension. Difficulties caused by contamination with thrombin-like enzymes can generally be obviated by using well-washed fixed platelets (which do not respond to thrombin) in the aggregation assay. Thrombin-like enzymes can be measured directly by adding aliquots of fractions to normal human plasma and measuring the clotting time in a clot timer or in a microtiter plate reader. The presence of contaminating botrocetin-like proteins in a venom fraction can be detected by the addition of small amounts of human vWF to the platelet suspensions.

If the presence of an alboaggregin in a fraction is assayed by resort to the alboaggregin's ability to compete with vWF for platelet binding, it is essential that fixed, rather than unfixed, platelets be used. The response of platelets to vWF is multifaceted. Initial binding of vWF to the platelet surface appears to be a relatively simple process. Extracellular $Ca^{2+}$ is not required for agglutination. When unfixed platelets are used, however, and when $Ca^{2+}$ is present the response to vWF can be more complex Although vWF binding does not itself induce platelet shape change, the cell-cell contact which occurs when platelets are agglutinated by vWF leads to the release of the constituents of platelet dense granules-including ADP, ATP, and serotonin. This process is associated with activation of platelet phospholipases and production of prostanoids, and involves stimulation of phosphoinositide turnover, release of inositol 1,4,5 triphosphate, and mobilization of intra-cellular $Ca^{2+}$. The thromboxane $A_2$ produced and the released ADP can cause other platelet responses such as shape change and binding of other plasma proteins, e.g., fibrinogen and fibronectin, and the release of granule constituents, including vWF. All of these secondary effects may be avoided by using fixed platelets to assay fractions containing purported alboaggregin activity for inhibition of platelet binding of labelled vWF. Platelets may be conveniently fixed with formalin, prepared from either a formalin solultion (Kirby and Mills, *J. Clin. Invest.* 56,491–502 (1975)), or paraformaldehyde (Alain et al., *J. Lab. Clin. Med.* 8, 318–328 (1975)).

Several galactose-specific lectins that agglutinate platelets have been reported in snake venoms. Their presence can be detected by inhibition of lectin-induced agglutination by galactose or other sugars. In order to determine whether the alboaggregins function as lectins, we examined the effects of eight different sugars (lactose, galactose, galactosamine, mannosamine, glucosamine, N-acetyl glucosamine, α-methyl glucoside and α-methyl mannoside) at concentrations up to 5 mg/ml. None of these sugars showed any effect on the binding of AL-B to platelets. AL-B did not agglutinate red blood cells, in contrast to several other platelet-agglutinating agents isolated from snake venoms (Ogilvie et al., *Thromb. Haem.* 62, 704–707(1989)); nor did $^{125}$I-AL-B bind to red blood cells. These results suggest that the alboaggregins are not lectins.

GPIb is found only on platelets, megakaryocytes and endothelial cells. Labeling of alboaggregin or cell-binding subunit thereof with a detectable label yields a reagent which may be used to detect the presence of these cell types in complex cell mixtures. Ready identification of platelets and megakaryocytes in peripheral blood smears or bone marrow aspirates is possible, as is detection of cultured endothelial cells in the presence of many other cell types which would not be identifiable by staining. The specificity and high affinity of the alboaggregins for the aforementioned cell types provides a considerable advantage over the morphological criteria and immunological techniques presently used to make these identifications.

Platelets adhere to damaged blood vessel walls via vWF, which binds to GPIb on the platelets. Bleeding disorders have been associated both with defects in vWF, e.g., von Willebrand's disease, and in platelet GPIb defects, e.g., Bernard-Soulier syndrome. The presence or absence of functional platelet GPIb in the patient's platelet specimen may be used to distinguish between these two causes of particular bleeding diathesis. The alboaggregins, since they only aggregate platelets containing intact GPIb, may therefore be used to test the presence of intact GPIb, and identify the bleeding disorder as arising from a vWF defect, versus a GPIb defect. The alboaggregins are in this regard more convenient and specific for detecting functional platelet GPIb than current diagnostic reagents, such as ristocetin or botrocetin, which are dependent on the presence of functional vWF, or on antibodies directed toward GPIb. Alternatively, functional GPIb may be detected using detectably-labelled alboaggregin or detectably-labelled platelet-binding subunit thereof, and assaying the platelets under study for binding by the labelled protein or subunit.

II. Purification of AL-A, AL-B, AL-C, and Echicetin

A. AL-A and AL-B1/AL-B2 Purification Procedure

The alboaggregins may be purified from available snake venoms, such as the venoms of *Trimeresurus albolabris, Bitis arietans,* and *Echis carinatus*. The following illustrates the purification of representative alboaggregins. Lyophilized *Trimeresurus albolabris* venom (IBF Biotechnics, Inc., Savage, Md.) was dissolved in 0.05 M-Tris buffer, pH 8.0 to a concentration of 20 mg/ml. Any undissolved material was removed by centrifugation at 12,000 g for two minutes, followed by filtration through a 0.45 micron filter. The crude venom was fractioned by high performance liquid chromatography (HPLC) on a Pharmacia Mono-Q column (Pharmacia LKB Biotechnology, Piscataway, N.J.; 5×50 mm) at a flow rate of 0.5 ml/min at room temperature. Proteins were eluted from the column using a linear gradient of sodium chloride (0—0.7 M) in 0.05 M Tris pH 8.0. Fractions were assayed for their absorbance at 226 nm and their ability to agglutinate formalin-fixed platelets as described above. We term the first peak, which eluted at about 0.24–0.26 M NaCl AL-A. The second peak, which has been termed AL-B, eluted from the column at about 0.34M NaCl. Chromatography under optimal conditions allowed resolution of AL-B into two active proteins which are similar in their size and biological activities. Characterization of amino acid sequences were primarily on the material derived from the first of these peaks, termed AL-B1.

Pooled crude AL-A was dialyzed against 1.8M ammonium sulfate in 0.05M Tris buffer, pH 8.0, and further purified by HPLC on a hydrophobic LKB TSK Phenyl-5PW column (Pharmacia LKB Biotechnology, Piscataway, NJ). This resulted in removal of a thrombin-like enzyme contamination from AL-A. Pooled crude AL-B was dialyzed against 0.05M Tris pH 8.0 and subjected to rechromatography on a Mono-Q column under the same Mono-Q conditions as above, in order to remove trace contaminants. Rechromatography removed a trace amount of fibrinogen-clotting activity from AL-B. The thus-purified active proteins were concentrated by dialysis against poly(ethylene glycol) 20,000 and then dialyzed against 0.05M Tris/0.15M NaCl pH 7.4. AL-A and AL-B comprise, res about 1.8% and 0.6% of the total venom proteins.

B. AL-C Purification Procedure

Lyophilized *Trimeresurus albolabris* venom purchased from Sigma Chemical Co. (St. Louis, Mo.) was fractionated on a Mono-Q column in 0.05M Tris buffer, pH 7.35, with a gradient from 0–0.7M NaCl. The last fraction, which had platelet agglutination activity, was named AL-C. Separation of small amounts of contaminants from AL-C was achieved by means of hydrophobic HPLC (Phenyl-5 PW column) with a linear gradient of ammonium sulfate (1.8M to 0M). Thus purified, AL-C was dialyzed in the same manner as for AL-A and AL-B. AL-C comprised about 0.11% of the total venom proteins.

Each of AL-A, AL-B and AL-C alboaggregins can be stored at 4° C. for several months without loss of activity.

C. Echicetin Purification Procedure

Lyophilized *E. carinatus* venom (Sigma Chemical Co., St. Louis, Mo.) was dissolved at 20 mg/ml in 0.1% (v/v) trifluoroacetic acid (TFA) (Fisher Scientific, Fair Lawn, N.J.). Undissolved components were removed by centrifugation. The supernatant was filtered prior to reverse-phase chromatography (Vydac TPRP C18, The Separation Group, Hesperia, Calif.) . The column was extensively washed with starting buffer (0.1% TFA) before elution with a linear gradient of 0 to 80% acetonitrile in 0.1% TFA. All fractions were lyophilized in a SpeedVac concentration (Savant Instrument Inc. Farmingdale, N.Y.) and redissolved in 100 μl of 0.05 M Tris-saline buffer, pH 7.4. They were assayed for their inhibitory effects on bovine vWF-induced agglutination of fixed platelets as described hereinafter. The active fractions from several preparations were combined and dialyzed against 0.05M sodium acetate buffer pH 5.0. The fraction eluting at 51% acetonitrile had most of inhibitory activity toward platelet agglutination induced by bovine vWF. Further purification of this fraction was carried out using a Mono-S column (5×50 mm, LKB Pharmacia) with a linear gradient from 0–0.6M NaCl gradient. All fractions were assayed for platelet agglutination inhibitory activity. Five fractions revealed inhibitory activity toward bovine vWF-induced platelet agglutination. The fraction that eluted at about 0.17M NaCl contained a majority of the activity. The active fractions from several preparations were pooled and concentrated by dialysis against solid polyethylene glycol 20,000 and then extensively dialyzed against 0.05M Tris-0.1M NaCl buffer, pH 7.4 . The homogeneous protein, termed "echicetin", was stored at 4 ° C. Performance of the purification steps in the reverse order (i.e., chromatography on Mono-S prior to chromatography on C8) yielded material of similar purity and activity.

Alternatively, crude venom is dissolved in 0.05M sodium acetate buffer, pH 5.0, then centrifuged and filtered to remove undissolved material. The soluble material is applied to a column of S-Sepharose Fast Flow (LKB-Pharmacia, Piscataway, NJ) at a ratio of approximately 200ml of gel per gram of crude venom. The column is washed with 0.05M sodium acetate, 0.15M NaCl pH 5,0, then eluted with a linear gradient from 0.15M NaCl to 0.35M NaCl in 0.05M sodium acetate, pH .5.0. Fractions containing activity are pooled and repurified on a Mono S column as described above, using a gradient from 0.15 to 0.27M NaCl.

D. Characterization and Proof of Alboaggregin Purity

Gel filtration chromatography was performed on a column (0.8×15 cm) of SEPHACRYL S-200 SUPERFINE (Pharmacia Fine Chemicals, Piscataway, N.J.) in 0.01M Tris/0.15M NaCl pH 7.4. Concentrated pure alboaggregin protein, mixed with a trace of corresponding $^{125}$I-labeled protein (see below) was loaded onto the column at a flow-rate of 0.1 ml/min. Fractions were assayed for radioactivity and tested for platelet agglutination activity. Single peaks of radioactivity were eluted from the column for AL-A and AL-B at positions characteristic of globular proteins with molecular weights of 40 and 23 kDa, respectively.

SDS-PAGE was performed on 12% polyacrylamide gels according to the method of Fling & Gregerson, Anal. Biochem. 155, 83–88 (1986), under reducing or nonreducing conditions (presence or absence of dithiothreitol) , using the following molecular weight standards (Sigma Chemical Co., St. Louis, Mo.) in order of decreasing molecular weight: bovine albumin (66 kDa) , ovalbumin (45 kDa) , glyceraldehyde-3-phosphate dehydrogenase (36 kDa) , carbonic anhydrase (29 kDa) , trypsinogen (24 kDa) , soybean trypsin inhibitor (20 kDa) , and α-lactalbumin (14 kDa). SDS-PAGE showed a single peak for each of the alboaggregin proteins, with mobilities corresponding to proteins with molecular weights of 45 kDa (AL-A), 23 kDa (AL-B), 100 kDa (AL-C) and 26 kDa (echicetin), respectively. Reduction prior to electrophoresis showed that each alboaggregin was composed of two chain types as shown in Table 1.

TABLE 1

| Alboaggregin | Molecular Weight by SDS Gel Electrophoresis | |
|---|---|---|
| | Non-reduced | Reduced |
| AL-A | 45 kDa | 18 kDa |
| | | 15 kDa |
| AL-B1 | 23 kDa | 17 kDa |
| | | 14 kDa |
| AL-B2 | 23 kDa | 17 kDa |
| | | 14 kDa |
| AL-C | 100 kDa | 20 kDa |
| | | 16 kDa |
| Echicetin | 26 kDa | 15 kDa |
| | | 13 kDa |

HPLC analysis of reduced AL-B revealed two peaks from AL-B and four peaks from AL-A, consistent with their being dimers and tetramers, respectively.

E. Amino Acid Sequencing

Samples of purified alboaggregins were subjected to amino acid sequencing essentially by the procedure described by Huang et al., Biochemistry 28, 661–666 (1989) as follows. Samples of purified alboaggregins were lyophilized and redissolved in approximately 100 microliters of 6M guanidine HCl solution containing 3 mM dithiothreitol, 5 mM EDTA and 50 mM Tris-HCl buffer, pH 8.6. The samples were incubated for 30–60 minutes under an argon atmosphere at room temperature in the dark. One microliter of vinyl pyridine was added and the incubation continued in the dark at room temperature for 30 minutes. For determination of internal amino acid sequences, proteins were fragmented by cyanogen bromide cleavage or protease digestion under standard conditions. The modified proteins or fragments were then separated from each other and the reagents by HPLC on C18-reverse phase column in 0.1% trifluoroacetic acid with a gradient of acetonitrile. Automated amino-terminal sequencing was performed on an Applied Biosystems Model 470A gas-phase sequencer coupled to an on-line PTH analyzer (Applied Biosystems Model 120A). Cysteine was detected as S-(pyridylethyl)cysteine. Sequencing indicated that each alboaggregin polypeptide chain has a distinct amino acid sequence, although there was considerable homology. In several of the sequences, the identity of one or more amino acid residues has not yet been determined. These positions are identified in the appended Sequence Listing by "Xaa".

It is believed that AL-A is a tetramer of non-identical polypeptide chains having the amino acid sequences of SEQUENCE ID NOS. 1, 2, 3 and 4, that AL-B is a dimer of nonidentical chains. The two polypeptide chains of AL-B1 have amino acid sequences of SEQUENCE ID NO: 5 and ID NO: 6. The two polypeptide chains of AL-B2 have amino acid sequences of SEQ ID NO: 7 and ID NO: 8. It is believed that AL-C is a hexamer, probably of two types of chains. The intact alboaggregins are compact structures, and migrate rapidly upon electrophoresis. Upon reduction, the molecules unfold to produce chains which run on electrophoresis at the true molecular weight.

Echicetin is believed to be a member of the alboaggregin family of proteins, since it shares many characteristics of AL-A, AL-B and AL-C. Echicetin is a dimer composed of two polypeptide chains with molecular weights similar to those seen in the other alboaggregins. The chains have amino acid sequences of SEQ ID NO:9 and ID NO:10. The amino acid sequences of the echicetin polypeptide chains show considerable homology to those of AL-A, -B and -C. Rabbit polyclonal antisera prepared against AL-B recognize not only AL-A, AL-B and AL-C, but also echicetin. Echicetin competes with AL-A, AL-B and AL-C as well as bovine vWF, for binding to fixed platelets. Binding of labelled echicetin to fixed platelets is inhibited by monoclonal antibody AK-2, directed against the 45 kDa N-terminal domain of glycoprotein Ib. Protease treatment of platelets to remove this domain abolishes echicetin binding.

For antithrombotic use, the native alboaggregins are subject to partial reduction to break the interchain disulfide bonds holding the component polypeptide chains together. Any suitable reducing agent capable of reducing cysteine-cysteine disulfide bonds to corresponding free sulfhydryl groups may be utilized. Preferably, reduction is achieved by means of treatment with dithiothreitol, a well-known disulfide bond reducing agent. The formerly multimeric molecule is thus caused to dissociate into its component polypeptide chains. In order to prevent reformation of the multimeric molecule, and restoration of agglutinating activity, the dissociated chains are treated with agents to block the now free cysteine sulfhydryl groups to prevent their re-oxidation. The individual monovalent chains retain the ability to bind platelets through GPIb, and inhibit platelet adhesion to exposed subendothelial elements, but without inducing platelet agglutination.

Alternatively, for antithrombotic use, echicetin may be used directly, since it inhibits vWF-associated platelet agglutination, but does not itself aggregate platelets.

Platelet agglutination by native intact alboaggregins is illustrated by the following experiment:

III. Platelet Agglutination by AL-B

A. Preparation of Platelet-rich Plasma and Washed Platelets

Blood was obtained from healthy normal donors who denied having taken any medication for two weeks. Blood was collected into acid citrate dextrose (1:8, v/v) and centrifuged at 150 g for 15 min. at room temperature to obtain platelet-rich plasma. Suspensions of washed platelets were prepared according to the method of Mustard et al., *Br. J. Haematol.* 22, 193-204 (1972) and suspended in Tyrode's solution (pH 7.35) containing 3.5 mg/ml bovine serum albumin (BSA).

B. Preparation of Formalin-fixed Platelets.

Fixed platelets were prepared as previously described by Kirby et al., *J. Clin. Invest.* 56, 491-502 (1975), from outdated platelet concentrates. Platelet concentrates were incubated with an equal volume of 2% formalin in Tris-saline buffer (0.01M Tris-HCl, 0.15M NaCl pH 7.4) overnight at 4° C. Platelets were then washed twice with Tris-saline buffer and suspended in Tris-saline buffer containing BSA to a BSA concentration of 10 mg/ml. Aliquots of these platelet suspensions were frozen at $-80°$ C. For each experiment, thawed platelets were diluted 1:10 with Tris-saline buffer without added BSA to an approximate platelet concentration of $3 \times 10^8$ platelets/ml.

C. Agglutination Studies

Agglutination of platelet-rich plasma, washed platelets and fixed platelets by AL-B was performed according to the method described by Kirby, *J Lab Clin. Med.* 100, 963-976 (1982). Platelet agglutination was assayed at 37° C. with constant stirring at 1200 RPM in an aggregometer and the extent of light transmission change was measured after two minutes. AL-B was added to suspensions of (A) fixed washed platelets or (B) washed platelets at final concentrations of (A) 0.2, 0.4, 0.6, 0.9 and 1.7 µg/ml and (B) 0.12, 0.24 and 0.48 µg/ml, respectively. The platelet concentration was approximately $3 \times 10^8$ platelets/ml in each suspension. AL-B agglutinated both fixed platelets and washed platelets in a dose-dependent manner. Once platelets were maximally agglutinated by AL-B, addition of bovine vWF gave no further response. AL-B also caused aggregation in platelet-rich plasma without causing platelet shape change or the release reaction. Polyanions, such as heparin and dextran sulfate, which strongly inhibit bovine vWF-induced platelet agglutination (Kirby & Mills, *J. Clin. Invest.* 56,491-502 (1975)), had no effect on AL-B-induced agglutination.

In similar experiments, AL-A and AL-C displayed similar platelet agglutination behavior. All three alboaggregins agglutinated platelet rich plasma and fixed platelets directly. To induce the same amount of platelet agglutination by bovine vWF, twice as much vWF was required to obtain the same change in light transmission. Microscopic examination of AL-induced platelet agglutination demonstrated that alboaggregins cause extensive formation of small aggregates, whereas bovine vWF induces coarse, macroscopic clumps, with few single platelets. Platelet agglutination activity of each of the alboaggregins was similar in terms of their $EC_{50}$ values.

Platelet agglutination induced by AL-A or AL-B was not inhibited by EDTA (10 raM), soybean trypsin inhibitor (0.5 mg/ml) N-ethylmaleimide, (10 raM) or $PGE_1$ (0.35 µM). The absence of proteolytic or fibrin-clotting activity from purified AL-A or AL-B, and the observation that several proteolytic enzyme inhibitors, including EDTA, soybean trypsin inhibitor, or N-ethylmaleimide, did not inhibit AL-B-induced platelet agglutination, indicates that AL-A or AL-B do not function as proteases to activate platelets.

The platelet agglutination studies indicate that the alboaggregins produce platelet agglutination directly without out the need for $Ca^{2+}+vWF$, or any other cofactor. In other experiments, monoclonal antibodies specific for vWF did not inhibit AL-B activity. It is clear from these results that AL-B binds to platelets in a manner distinct from botrocetin, and that the alboaggregins are therefore distinct from botrocetin. In contrast to botrocetin, which acts in a two-step manner, first binding to vWF to form a complex, which then binds GPIb to cause agglutination, the alboaggregins directly produce platelet aggregation without the need for vWF.

IV. Alboaggregin and Echicetin Labeling

The alboaggregins or subunits thereof may be detectably labeled using any of the known protein labels. The label is detected by a physical or chemical means. Such labels include radiolabels; chromophoric labels such as a fluorescent, ultraviolet-absorbing, or visible light-absorbing labels; enzyme labels, etc. For enzyme-linked immunosorbent assays, the label is an enzyme, e.g., alkaline phosphatase which cleaves a chromogenic substrate to release a chromophoric product.

The label may be attached to the alboaggregin molecule indirectly. For example, the label may be affixed to a monoclonal or polyclonal antibody or F(ab) fragment which binds alboaggregin, but does not interfere with its platelet-binding or platelet-aggregating activity.

According to one embodiment, the detectable alboaggregin label comprises a radioactive isotope, preferably a radioactive iodine isotope. The radiolabeling procedure is illustrated as follows.

AL-B was labeled by the so-called chloramine T procedure of Bocci, *Int. J. Appl. Rad. and Isotopes* 15, 449–456 (1964), as follows. Purified AL-B (approximately 4.4 nanomoles in 0.5 ml 0.05M Tris buffer pH 8.6) was mixed with 200 $\mu$Ci Na$^{125}$I and 4 nanomoles of unlabeled NaI. Iodination was initiated by the addition of chloramine T (0.9 $\mu$moles) and terminated after 10 seconds by the addition of sodium metabisulfite (1.2 $\mu$moles). Labeled AL-B contained approximately $1-3\times 10^9$ counts per minute (cpm) per rag. Von Willebrand Factor and echicetin were labeled by the Iodogen procedure, as previously described by Kirby, *J. Clin. Invest.* 56, 491–502 (1975). Labeled proteins were separated from free Na$^{125}$I and iodotyrosine on disposable columns of Sephadex G-25. The extent of labeling was determined by precipitation of protein with 10% trichloroacetic acid. After purification, the labeled proteins showed less than 5% unbound $^{125}$I.

Echicetin was labeled by the IodoGen procedure (Kirby, *J. Lab. Clin. Med.* 100:963 (1982)) Purified echicetin (1 3 nanomoles) was added to a vial that had been coated with 50$\mu$g of IodoGen (Pierce Chemical Co.). The reaction mixture was incubated for 10 minutes at room temperature with gentle agitation. The reaction was stopped by adding 100 $\mu$l of a saturated solution of tyrosine.

The specific activity of labeled proteins were between 0.3 and $1.0\times 10^9$ CPM/mg. $^{125}$I-echicetin migrated with the same mobility as unlabeled echicetin on SDS-gel electrophoresis.

V. $^{125}$I-Alboaggregin and $^{125}$I-vWF Binding to Platelets

The alboaggregins bind platelets with high affinity. Alboaggregin binding of platelets is illustrated as follows.

Binding of $^{125}$I-bovine vWF and 125I-alboaggregins to labeled platelets was carried out according to Kirby, *J. Lab. Clin. Med.* 100, 963–976 (1982). Platelets were diluted and incubated at 37° C. for at least 10 min. prior to performing binding studies. Radiolabeled proteins were diluted in Tris-saline buffer containing 1 mg/ml of BSA and preincubated with buffer or a sample to be tested for inhibitory activity. The platelet suspension ($1.9\times 10^8$ platelets/ml) was added to the radiolabeled protein (26 ng/ml) and incubated at 37° C. for different periods of time. Unlabeled AL-B (1.8 $\mu$g/ml or 8.6 $\mu$g/ml) was added to duplicate suspensions after 5 min. of incubation with $^{125}$I-AL-B. Platelets were separated from free ligand by centrifugation for 4 min. at 12000 g. Supernatant and pellets were counted in an INTERTECHNIQUE gamma counter to determine the amount of free and platelet-bound radioactivity, respectively. Nonspecific binding (2–4% of total radioactivity) was determined in the presence of an excess of unlabeled AL-B. Binding affinities were determined by Scatchard analysis, using the LIGAND program (G.N. McPherson, Cambridge, U.K.). In experiments where inhibition of binding was measured, the total amount of labeled protein bound in the absence of inhibitor was defined as 100%.

The binding of $^{125}$I-echicetin was similarly investigated. Labelled protein was diluted in 0.05M Tris-saline buffer containing 1 mg/ml of BSA and preincubated with either buffer or unlabelled proteins prior to addition of 300 $\mu$l platelet suspensions ($3\times 10^8$ platelets/ml). The mixtures were allowed to incubate at 37° C. for five minutes. Bound proteins were separated from free proteins by centrifugation for 2 minutes at 12,000 g. The supernatants were carefully removed by a capillary glass pipet. Binding affinities were determined by Scatchard analysis, as performed for AL-B. Scatchard analysis of echicetin binding to fixed platelets was performed with the radioligand binding analysis programs (LIGAND) by G.A. McPherson (Elsevier-BIOSOFT, Cambridge UK).

The results of the above binding studies with AL-B indicate that AL-B was labeled with $^{125}$I without loss of its platelet-agglutinating activity. Radiolabeled AL-B comigrated with unlabeled AL-B on SDS-PAGE. Labeled AL-B bound directly to platelets in an unstirred system. The half-time for binding was less than 15 seconds, and the binding was more than 90% complete by 1 min. Binding was rapidly reversible as shown by the ability of excess unlabeled AL-B to remove previously bound AL-B. 50% of the maximal specific binding occurred at an AL-B concentration of about 0.3 $\mu$g/ml. Scatchard binding analysis revealed one class of binding site for AL-B on fixed platelets in platelet-rich plasma, with a $K_d$ of approximately 13.6 $\pm$9.3 riM. The data indicate approximately 30,800$\pm$14,300 binding sites for AL-B on each platelet.

Similar results were obtained from the study of $^{125}$I-echicetin binding to platelets. Echicetin binding reached a maximum within 10 seconds. The binding was reversible by unlabelled echicetin (1 $\mu$g/ml). Fifty percent of maximal specific binding of $^{125}$I-echicetin to platelets occurred at approximately 0 5 $\mu$g/ml (19 nM) Scatchard binding analysis from three similar experiments revealed one class of binding sites for echicetin on fixed platelets with a $K_d$ of approximately 30 $\pm$1.8 nM. The data indicate approximately 45,000 +2400 binding sites per platelet.

Further experiments were conducted to determine the relationship of the alboaggregin-binding site to the vWF binding site on platelets. Unlabeled AL-B and bovine vWF were analyzed for their ability to compete with either labeled AL-B or labeled bovine vWF for binding to platelets. $^{125}$I-AL-B (6.7 ng/ml) was mixed with varied concentrations of either unlabeled AL-B or unlabeled vWF. $^{125}$I-Bovine vWF (0.57 $\mu$g/ml) was mixed with either unlabelled AL-B or unlabeled bovine vWF. Binding of radioactivity to fixed platelets was measured by centrifugation and expressed as a percent of the control value obtained in the absence of any unlabeled protein. Approximately 0.8 $\mu$g of unlabeled AL-B was required for 50% inhibition of $^{125}$I-AL-B binding to platelets. In contrast, bovine vWF showed only a very weak inhibition of $^{125}$I-AL-B binding to platelets. Approximately 0.2 $\mu$g/ml of unlabeled AL-B caused 50% inhibition of vWF binding to platelets, while about 10 $\mu$g/ml of unlabeled bovine vWF were required for 50% inhibition of labeled vWF binding.

These results suggest that the binding domain for AL-B on platelet GPIb is close to or identical with the binding site for vWF, but that AL-B has a higher affinity (on a per μg basis) than vWF.

The binding of AL-A and AL-C to platelets was measured in the same manner in order to compare their platelet binding abilities with that of vWF. $^{125}$I-AL (AL-A, AL-B and AL-C) and bovine vWF directly bound to platelets at approximately 45%, 25%, 78% and 15% of total radioactivity added, respectively. All unlabeled alboaggregins completely competed the binding of $^{125}$I-bovine vWF to platelets. AL-B and AL-C compete with each other effectively. AL-A had a weak competitive capacity on the binding of labeled AL-B and AL-C. The extent of competition of each alboaggregin is presented in FIGS. 3-6 and summarized in Table 2:

TABLE 2

Competitive Binding of $^{125}$I-Ligands to Platelets

| $^{125}$I-Ligand | Competing unlabeled ligands (IC$_{50}$ μg/ml) | | | |
|---|---|---|---|---|
| | AL-A | AL-B | AL-C | bovine-vWF |
| AL-A | 2.3 | 0.4 | 1.7 | >10 |
| AL-B | 4.6 | 0.8 | 1.0 | >10 |
| AL-C | 1.4 | 0.2 | 0.3 | >10 |
| bovine-vWF | 1.0 | 0.2 | 0.2 | 2.1 |

FIGS. 3-6 show the competition between alboaggregins and bovine vWF for binding to platelets. The labelled proteins in FIGS. 3, 4, 5 and 6 were bovine vWF (36 ng/ml), AL-A (54 ng/ml), AL-B (26 ng/ml) and AL-C (59 ng/ml), respectively (bovine vWF (▲—▲), AL-A (O—O), AL-B (●—●) and AL-C (∇—∇)).

Echicetin likewise is a strong competitor of vWF for binding to platelets. Bovine vWF only weakly inhibits the binding of $^{125}$I-echicetin to platelets (IC$_{50}$ >20 μg/ml). Echicetin strongly inhibited the binding of $^{125}$I-bovine vWF to fixed platelets, with an IC$_{50}$ of only 0.2 μg/ml Echicetin has a platelet-binding affinity similar to that of AL-B. Binding of $^{125}$I-echicetin to GPIb was competed by unlabeled echicetin and by AL-B at approximately identical concentrations (IC$_{50}$ >0.5 μg/ml).

VI. Interference of Alboaggregin Platelet Binding and Platelet Aggregation by Monoclonal Antibody to GPIb 45-kDa N-terminal Domain Antibodies against the 45 kDa fragment from the N-terminal domain of GPIb inhibit the response of platelets to vWF (Wicki & Clemetson, Eur. J. Biochem. 153, 1-11 (1985); Handa et. al., J. Biol. Chem. 261, 12579-12585 (1986)). We found that these antibodies also inhibited the platelet binding and agglutinating activity of the alboaggregins, thus indicating that the platelet binding domain for the alboaggregins is also in the 45 kDa N-terminal domain of GPIb.

The following inhibitory effect study on fixed platelets was performed with monoclonal antibodies AK1, AK2, AK3 and FMC 25, all obtained from the Research Center for Thrombosis and Cardiovascular Disease, Department of Medicine, University of Sydney, Westmead, NSW, Australia. AK1 is directed against an epitope on the membrane-associated region of the GPIb-IX complex; AK2 is directed against the 45 kDa N-terminal peptide of GPIb; AK3 is directed against epitopes on the macroglycopeptide region of the GPIb-IX complex; FMC 25 is directed against GPIX (Berndt et al., Biochemistry 27, 633-640 (1988)). In brief, 400 μl of platelet suspension was preincubated with 10 μl of antibody at varied concentration for 1 minute prior to addition of 10 μl of alboaggregin or bovine vWF. The extent of light transmission change was measured after 2 minutes. In a binding experiment, monoclonal antibodies at varied concentration were preincubated with $^{125}$I-AL prior to mixing with fixed platelets. We found that monoclonal antibody AK2 completely inhibited both the binding of radiolabeled ALs to platelets and the platelet agglutination induced by ALs. Monoclonal antibodies AK1, AK3, and FMC 25 had no inhibitory effect. In another experiment, 300 μl of fixed platelet suspension (4×10$^8$ platelets/ml) were preincubated with varied concentration of monoclonal antibody AK2 for 10 minutes at room temperature. The platelet suspensions were then warmed to 37°C. The platelet binding of the following amounts of radiolabeled alboaggregin or vWF was measured: 12 ng/ml $^{125}$I-AL-A (O—O); 22 ng/ml of $^{125}$I-AL-B (●—●); 31 ng/ml of $^{125}$I-AL-C (△—△); and 56 ng/ml of $^{125}$I-bovine vWF (▲—▲). The results are set forth in FIG. 1.

In yet another experiment, 400 μl of platelet suspensions were warmed to 37° C. in an aggregometer for 5 minutes. 10 μl of varied concentrations of monoclonal antibody AK2 were added to the platelet suspension prior to addition of AL or bovine vWF and measurement of the rate of platelet agglutination. The results are set forth in FIG. 2.: AL-A (O—O); AL-B (▲—▲); AL-C (△—△); bovine vWF (▲—▲).

Figure 2:
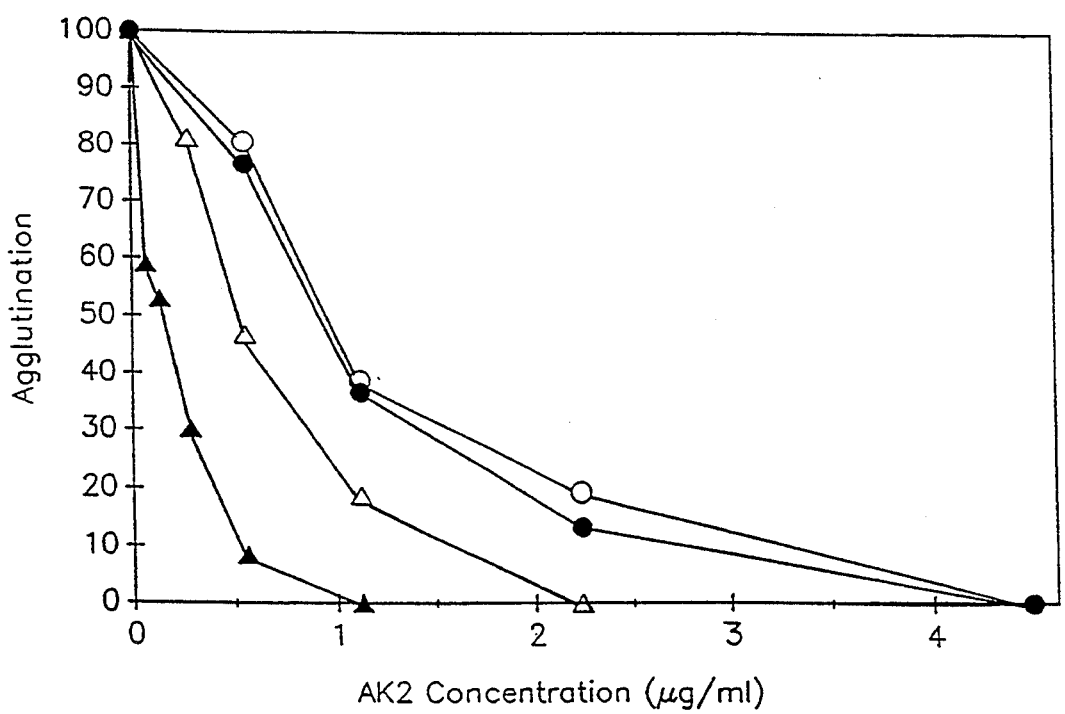
FIG. 2 is a plot of the inhibitory effect of monoclonal antibody AK2 on platelet agglutination induced by alboaggregin or bovine vWF: AL-A (○—○); AL-B (●—●); AL-C (△—△); bovine vWF (▲—▲).
Figure 3:
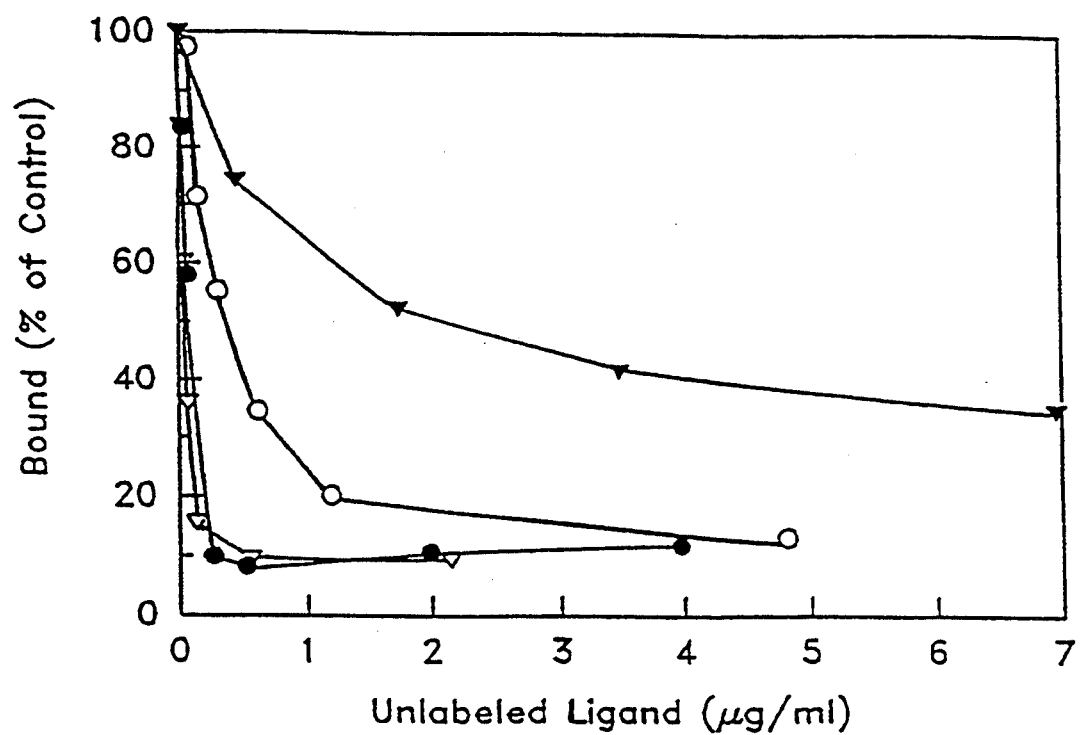
FIG. 3 is a plot of the competition between alboaggregins and bovine vWF for binding to platelets. The radio-labelled bovine vWF (36 ng/ml) was preincubated with varied concentrations of unlabeled proteins (bovine vWF (▼—▼), AL-A (○—○), AL-B (●—●) and AL-C (△—△)) prior to addition of platelet suspensions. Control binding was measured in the absence of any unlabelled competitor. Values are averages from duplicate samples.
Figure 4:
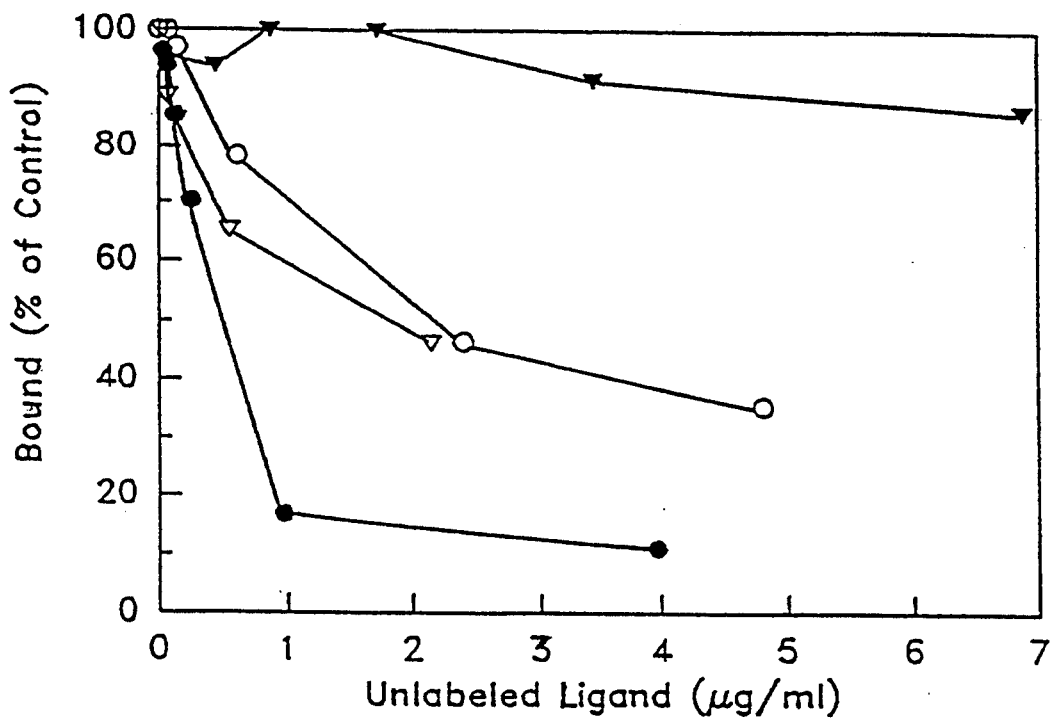
FIG. 4 is similar to FIG. 3, except that the radiolabelled protein was AL-A (54 ng/ml).
Figure 5:
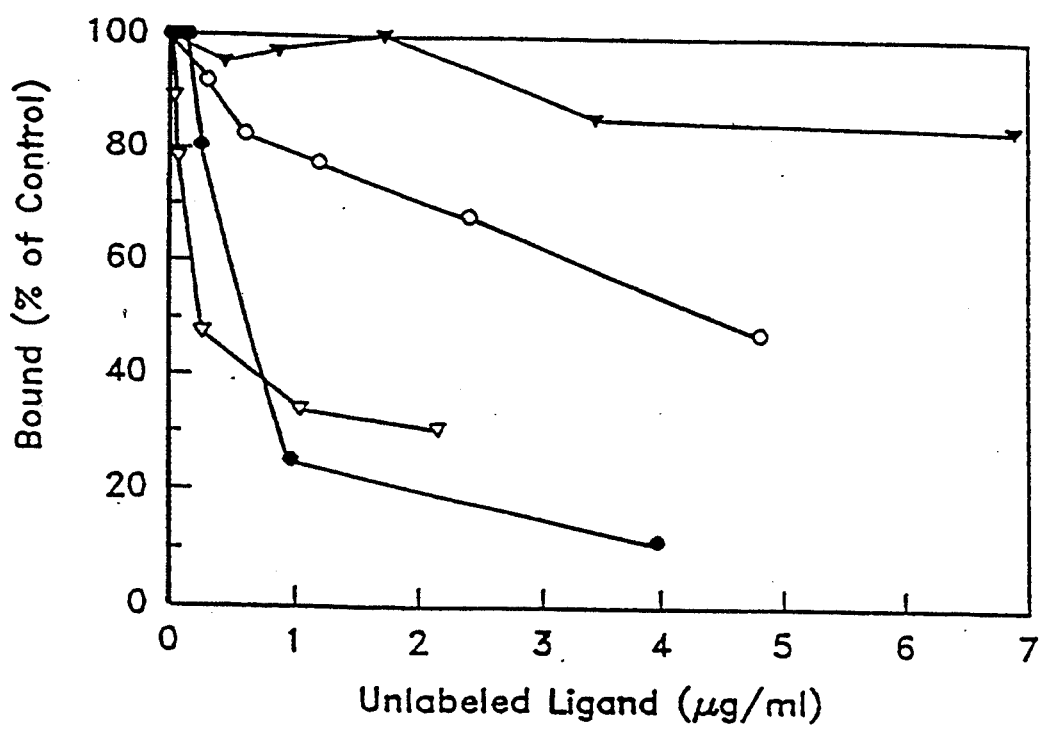
FIG. 5 is similar to FIG. 3, except that the radiolabelled protein was AL-B (26 ng/ml).
Figure 6:
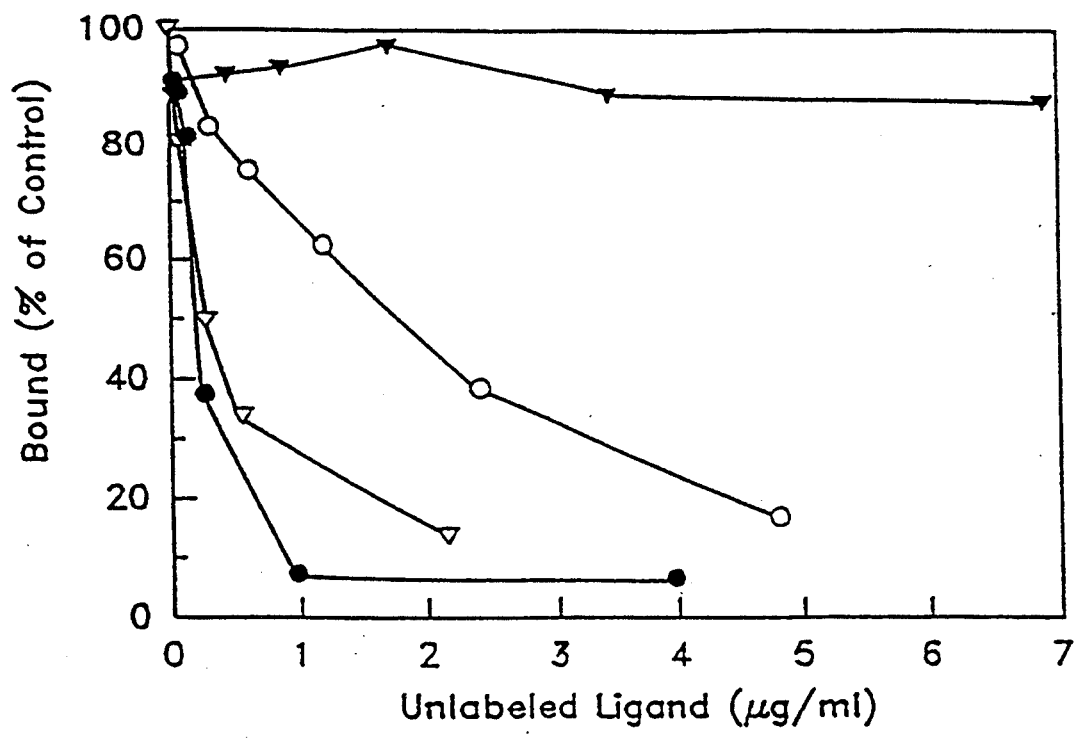
FIG. 6 is similar to FIG. 3, except that the radiolabelled protein was AL-C (59 ng/ml).

From FIGS. 1 and 2, 0.5 μg/ml and 1.0 μg/ml AK2 was required to obtain 50% inhibition of platelet agglutination and AL-B binding, respectively. Since the alboaggregins can compete efficiently with bovine vWF for binding to platelets, this further suggests that vWF and the alboaggregins have either the same or closely adjacent binding sites on GPIb.

In control experiments, monoclonal antibodies to GPIIb/IIIa, to bovine vWF, and to bovine serum albumin had no effect on the binding of AL-B to platelets.

VII. Alboaggregin Binding and Agglutination Of Elastase-treated Platelets

The enzyme elastase cleaves GPIb to release the 45 kDa N-terminal peptide which has been proposed to contain the vWF-binding domain (McGowan & Detwiler, Blood 65, 1033-1035; (1985); Cooper et al., J. Lab. Clin. Med. 90, 512-521 (1977)). Elastase (Elastin Products Co., Inc., Pacific, Mont.) was diluted with Tris-saline buffer and added to fixed platelets at different concentrations (0.008 μg-0.7 μg). Platelet suspensions (3×10$^8$/ml) were incubated with the elastase for 5 min. at 37° C. Digestion was stopped by the addition of a 5-fold excess of α$_1$-antitrypsin. Binding of labeled proteins and platelet agglutination were measured as described above. The binding of both $^{125}$I-AL-B and $^{125}$I-bovine vWF to platelets was inhibited by this elastase treatment. Platelet agglutination was inhibited in a similar manner. These results further indicate that the alboaggregins bind platelets at or near the vWF binding domain.

VIII. Determination of Binding Domain For Echicetin on Platelets GPIb

Monoclonal antibody AK2, which is directed against the 45 kDa N-terminal domain of GPIb, strongly inhibited the binding of echicetin and bovine vWF to fixed platelets with IC$_{50}$'s of 0.8 μg/ml and 0.3 μg/ml respectively. Monoclonal antibodies AK3 and AK1 (against epitopes on the macro-glycopeptide region of GPIb and the membrane-associated region of the GPIb-IX complex) and FMC 25 (directed against GPIX) had no effect on binding of echicetin to platelets.

IX. Echicetin Inhibition of Washed and Fixed Platelet Agglutination

Figure 7:
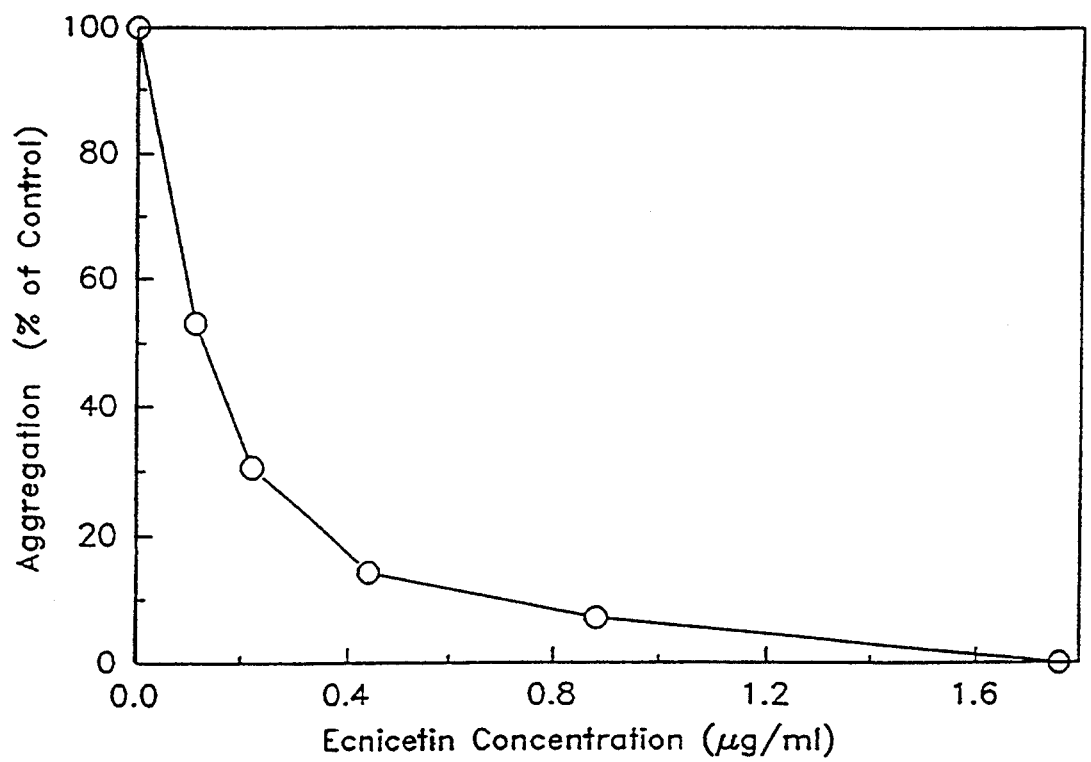
FIG. 7 is a plot of the dose-dependent inhibitory effect of echicetin on bovine vWF-induced aggregation of washed platelets.

Aggregation of washed platelets induced by bovine vWF was inhibited by echicetin in a dose-dependent manner, according to the following experiment. Aliquots of 0.4 ml of washed platelets, suspended in Tyrode's buffer ($3.0 \times 10^8$ platelets/ml), were incubated in an aggregometer cuvette for 1 min. at 37° C. prior to addition of either 10 µl Tyrode's buffer or 10 µl echicetin (0–1.8 µg/ml). After one min. incubation, 10 µl of bovine vWF (3.1 µg/ml) was added. Agglutination measured in the absence of echicetin was defined as 100%. The results are shown in FIG. 7.

Figure 8:
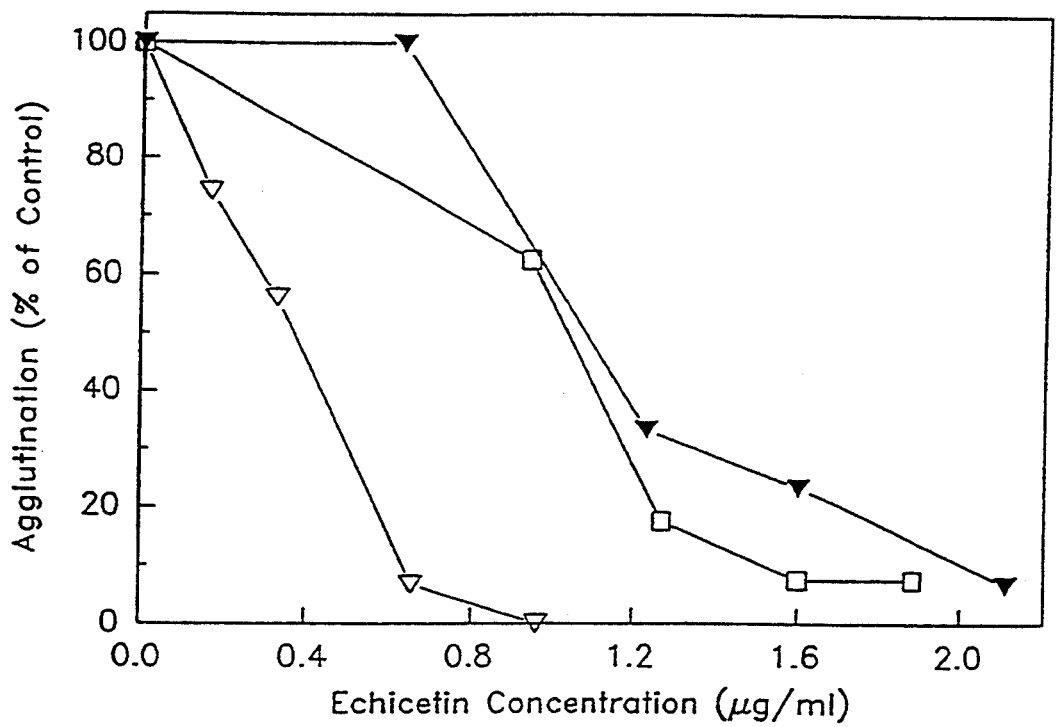
FIG. 8 is a plot of the dose-dependent inhibitory effect of echicetin on agglutination of fixed platelets induced by human vWF (▲—▲), bovine vWF (▽—▽) or AL-B (□—□).

Echicetin also inhibited agglutination of fixed platelets induced by bovine vWF, AL-B or by human vWF in the presence of botrocetin (FIG. 8). Aliquots of fixed platelets ($3.1 \times 10^8$ platelets/ml) were preincubated with 10 µl 0.05M Tris - 0.1M NaCl buffer or 10 µl echicetin for 1 min. prior to addition of human vWF (4.15 µg/ml with botrocetin (2.3 µg/ml ▼—▼), bovine vWF (w.9 µg/ml ▽—▽) or AL-B 0.9 µg/ml □—□). Platelet agglutination induced by human vWF, bovine vWF or ALB without echicetin was defined as 100%.

The concentrations of echicetin required for 50% inhibition of bovine vWF-induced agglutination of washed or fixed platelets were approximately 0.15 µg/ml and 0.4 µg/ml, respectively. The concentrations of echicetin for the same amount of inhibition of agglutination of fixed platelets induced by botrocetin/human vWF or AL-B were about 1.1 µg/ml and 1.05 µg/ml, respectively.

Echicetin had no effect on aggregation of washed platelets by ADP (10 µM) in the presence of fibrinogen (0.24 mg/ml).

X. Reduction of Echicetin

Purified echicetin (2.9 µM) was mixed with DTT (1.5 mM–32 mM) in 0.05M Tris-0.1M NaCl pH 7.4 at 37° C. for 30 min. A twofold excess of iodoacetamide (IAA) in 0.05M Tris buffer pH 8.6 was then added in the dark to block the newly generated sulfhydryl groups. The mixture was allowed to stand at 22° C. for 30 min. in the dark. Reduction of echicetin was confirmed by SDS-gel electrophoresis and autoradiography. The reduced echicetin was tested for its ability to compete with unreduced $^{125}$I-echicetin for binding to platelets. Reduction of echicetin did not destroy its binding activity. Reduction of $^{125}$I-echicetin by DTT (0.08 mM–16 mM) and alkylation by IAA under similar conditions was confirmed by SDS-gel electrophoresis and autoradiography.

XI. Measurement of Binding of $^{125}$I-Echicetin to Erythrocytes and Neutrophils While echicetin strongly binds to platelets, it does not bind significantly to erythrocytes or neutrophils.

Human erythrocytes were isolated by centrifugation of blood at 500 g for 15 min. The erythrocytes were used as a 3% suspension in 0.05M Tris-saline buffer. Human neutrophils were prepared as described in Eggleton et al., *J. Immunol Methods*, 121:105 (1989), by overlaying human ACD blood on a solution of sodium metrizoate and Dextran 500 (Polyprep$^{198}$) (Nycomed, Oslo, Norway) and centrifuging at 400 g for 30 min. Residual erythrocytes were lysed with isotonic ammonium chloride. Cell viability was shown by trypan blue exclusion. The concentration of neutrophils was $3.7 \times 10^7$/ml. Binding of $^{125}$I-echicetin to erythrocytes and neutrophils was measured by the same procedure as the binding of $^{125}$I-echicetin to platelets. In the assay mixture, $^{125}$I-echicetin (70 ng/ml) and 25 µl of buffer or unlabeled echicetin (4.3 µg/ml) were added to 200 µl of cell suspension. Total binding and nonspecific binding were determined in the absence or presence of unlabeled echicetin, respectively.

$^{125}$I-echicetin did not bind significantly to either human erythrocytes or neutrophils. The percentages of total binding and nonspecific binding were 1.23% and 1.1% for neutrophils, and 3.16% and 2.06% for erythrocytes, respectively.

XII. Effect of Echicetin on Bleeding Time in Mice

The platelet aggregation inhibitory effect of echicetin was observed in vivo by prolongation of bleeding time in mice. The disintegrin echistatin, which inhibits platelet aggregation by blocking the platelet GPIIb/IIIa receptor, was used as a positive control.

$CD_1$ mice (male and female 25–27 g body weight) were obtained from Charles River (Wilmington, Mass.). Mice were kept at a 12 hour light interval and fed with conventional food and water ad libitum. The guidelines for the use of animals in biomedical research were followed according to "International Committee Communications Guidelines", Giles, *Thromb. Haemost.* 58:1078 (1987).

Four groups of mice were intravenously injected with echicetin at different concentrations. Another group of mice (n=4) was intravenously injected with echistatin (2.0 µg/mouse). Bleeding time of mice was measured by a modification of the method described by Dejana et al., *Thromb. Haemost.* 48:108 (1982). Solutions of either Tris-saline buffer or the various concentrations of echicetin or echistatin in a total volume of 0.2 ml were injected intravenously through a lateral tail vein of the mouse. A cut of 3–4 mm from the tail tip of mouse was done one minute after injection. Immediately, the mouse's tail was passed through a restraining tube and inserted into a container filled with saline at 37° C. Bleeding time was recorded from when bleeding started until it had completely stopped for more than 30 seconds. Bleeding times longer than 10 min. were not recorded.

The platelet count before and after echicetin injection was measured. Blood (10 µl) was obtained by a puncture of tail vein at a different spot from the one used for injection of echicetin. Blood was diluted with the Unopette System (Becton Dickinson) and platelets were counted by phase-contrast microscopy.

The bleeding time of control mice (injected with buffer) was $1.54 \pm 0.32$ min (n=9). Bleeding times of three other groups of mice that were injected with various concentrations of echicetin (0.1, 0.5 and 2.0 µg per mouse) was significantly prolonged ($2.96 \pm 1.17$ min, >10 min, >10 min., respectively). The disintegrin echistatin (2.0 µg/mouse) also caused a prolongation of bleeding time similar to echicetin. Platelet counts dropped from $112 \pm 17.5 \times 10^6$/µl before injection to $44.5 \times 10^6$/5 min. after injection of echicetin, 0.25 µg/mouse (40% of initial value). Platelet counts increased thereafter to $52.5 \pm 14 \times 10^6$/µl 30 min. after injection (47% of initial value) and $75.3 \pm 11.6 \times 10^6$/µl 60 min. after injection (67.2% of initial value), respectively.

XIII. Therapeutic Application

It is contemplated that modified alboaggregins, produced by partial reduction, proteolytic fragmentation, or amino acid modification or substitution will bind to platelet GPIb to inhibit vWF binding thereto, without inducing substantial platelet aggregation. Thus, the isolated polypeptide chains are useful as antithrombotic agents for inhibiting platelet adhesion to exposed subendothelial components of blood vessel walls. The size of the isolated alboaggregin polypeptide chains indicates that they should have a half-life in circulation of 10–60 minutes, by analogy to other snake venom polypeptides of similar size. The polypeptides of the invention are thus suitable for acute administration. Since alboaggregins bind to non-activated platelets, the platelets may serve as carriers, and further prolong the effective circulation half-life. Most importantly, the polypeptides of the invention cause specific blocking of GPIb-mediated platelet responses, i.e., platelet adhesion, thereby causing passivation of platelets. However, since the AL polypeptides act specifically by inhibiting platelet adhesion to subendothelial elements via vWF, they will not block responses of platelets to other agents such as ADP, thrombin, thromboxane, etc. Thus, administration of the polypeptides of the invention should not give rise to bleeding complications.

The alboaggregin polypeptides are water-soluble, and are stable to sterile filtration and lyophilization. They may be stored as either lyophilized powders or sterile solutions in isotonic buffers, with appropriate stabilizers as necessary to preserve maximum activity and shelf-life. The alboaggregin polypeptides may be administered in any situation where inhibition of human or mammalian platelet aggregation or adhesion is desired. Platelet adhesion and aggregation is a consequence of invasive medical techniques which cause epithelial damage and exposure of the subendothelial elements. The polypeptides may find utility in surgery on peripheral arteries, open heart surgery, angioplasty or other procedures where damage to the endothelial wall of blood vessels may trigger platelet adhesion and aggregation. The polypeptides may be administered to patients undergoing these techniques to prevent platelet aggregation and the formation of thrombi.

Unlike AL-A, -B and -C, intact echicetin does not induce platelet aggregation. Hence, it may be used to inhibit vWF binding to platelets without first undergoing partial reduction.

The alboaggregin polypeptides are most effectively administered intravenously. Since the polypeptides are soluble in water, they may therefore be effectively administered in solution. For intravenous administration, they may be dissolved in any appropriate intravenous delivery vehicle containing physiologically compatible substances, such as sodium chloride, glycine and the like, having a buffered pH compatible with physiologic conditions. Such intravenous delivery vehicles are known to those skilled in the art.

The amount of polypeptide administered will depend on the individual clinical circumstances. Based upon our observation that approximately 0.2 μg/ml AL-B is sufficient to cause 50% inhibition of vWF binding to platelets, it is believed that approximately 0.5 mg of an alboaggregin single polypeptide chain with a platelet binding affinity equal to that of AL-B will be therapeutically effective, based upon a 2500 ml plasma volume of a human subject weighing 70 kg. More or less alboaggregin polypeptide may be administered as needed.

XIV. Alboaggregin Molecular Cloning

Purification of the alboaggregins to chemical homogeneity has permitted amino acid sequencing of the constituent polypeptide chains. It is contemplated that the alboaggregin polypeptide chains may be prepared through genetic engineering techniques, utilizing either partial or complete amino acid sequence information. It is thus understood that the scope of the invention is not limited to polypeptides isolated by following the chromatographic procedures disclosed herein, but also includes alboaggregin polypeptides as they may be prepared by genetic engineering techniques.

Based upon a complete amino acid sequence, one may prepare a synthetic gene corresponding to the sequence and introduce the gene into an appropriate host by cloning vectors. Alternatively, it is contemplated that alboaggregin polypeptides may be obtained by recombination and cloning of the appropriate native gene obtained from venom producing cells.

Based upon at least a partial amino acid sequence, such as the partial or complete sequences disclosed herein for the constituent polypeptide chains of AL-A, AL-B and echicetin, one may prepare suitably labeled synthetic oligonucleotide probes for screening a cDNA library prepared from snake venom glands. An appropriate cDNA library may be prepared according to any of the known techniques for preparing such libraries, such as the techniques described in Chapter 8 of *Molecular Cloning: A Laboratory Manual*, Second Edition, 1989 (J. Sambrook, E.F. Fritsch and T. Maniatis, editors). According to one methodology, a cDNA library is prepared from polyA+mRNA using a snake venom gland. The library is constructed using, for example, the insertion vector λZAPII (Stratagene, La Jolla, Calif.) which is equipped with multiple cloning sites within plasmid sequences that can be excised in vivo and converted to a plasmid vector, Bluescript SK (M13-). λZAPII carries a polycloning site downstream from the *E. coli lacZ* promotor. See the map of λZAP/R in *Molecular Cloning*, supra, at page 2.52. λZAPII is equivalent to λZAP except that the Sam100 mutation has been removed to allow better growth of the bacteriophage, which, in turn, causes the plaques to become blue much sooner. cDNAs up to 10kb in length may be inserted into the λZAPII polycloning site and expressed in either infected bacteria or induced lysogens. The Bluescript SK(M13-) plasmid carrying the cloned DNA is excised in the presence of fl or M13 helper bacteriophages, e.g., fl R408 (Russel et al., Gene 45:333 (1986)).

According to one embodiment, λZAPII containing a cDNA library generated from snake venom gland genetic material is mixed and incubated with a plating bacteria, e.g. NM522, suitable for propagation of the λZAPII bacteriophage, and grown on agar plates. The plaques are transferred to nitrocellulose filters when they reach a diameter of approximately 1.5 mm. The phage are lysed, washed and fixed to the nitrocellulose filters and hybridized overnight at 42° C. using appropriate $^{32}$P-labeled probes for alboaggregin genes. The probes may take the form of oligonucleotides synthesized on the basis of the least degenerate portions of the purified alboaggregin polypeptides. The oligonucleotides are endlabeled to high specific activity with $^{32}$P using T4 polynucleotide kinase and gamma$^{32}$P-ATP. The nitrocellulose filters are dried following hybridization with oligonucleotide probe, and then autoradiographed to identify positive clones.

Plaques containing positive clones are recovered from the agar plates and treated with chloroform to release the λ-particles. Suitable host bacteria are coinfected with the release λ-particles and a helper phage, e.g., R408. Following incubation, the mixture is heated to kill the bacteria and inactivate the parent λZAPII, but not packaged Blue-script phage particles containing single stranded DNA (ssDNA) which are present in the supernatant following centrifugation. The ssDNA is isolated by standard methods well-known to those skilled in the art and analyzed by electrophoresis on agarose gels following EcoR1 digestion of the DNA to determine the size of the selected cloned inserts.

The identity of clones corresponding to alboaggregin mRNA is verified by excising ssDNA from the selected clones, as described above. The ssDNAs are $^{32}$P-labeled and used as hybridization probes under high stringency conditions in Northern blot analysis of mRNA purified from the appropriate snake venom gland, i.e., *Trimeresurus albolabris* gland. Detection of mRNA transcripts of approximately 0.5 kb and 1.4 kb in the Northern blot indicates transcript sizes similar to those of the 13 kDa and 50 kDa alboaggregins, respectively. The mRNA identified by Northern blotting is recovered, solubilized and translated in vitro according to known techniques. The translated protein is then analyzed by SDS-PAGE, and then Western blotted and tested for biological activity as described elsewhere herein.

DNA from the final selected clone(s) is sequenced using the Sanger dideoxy-mediated chain termination method utilizing oligonucleotide primers according to standard published methodologies (Sambrook, et al. *Molecular Cloning*, (1989)). Following DNA sequencing, correspondence between portions of the deduced amino acid sequence obtained from the nucleotide sequence of the cDNA and the partial or complete amino acid sequences of alboaggregin polypeptides derived from authentic snake venom protein are determined.

In this manner, DNA sequences coding for any of the alboaggregin polypeptide chains is generated, particularly the polypeptides comprising SEQUENCE ID NO:1 through NO:10.

It is contemplated, based upon the available alboaggregin amino acid sequences, that analogs thereof may be prepared and effectively screened for ability to compete with vWF for binding to platelets according to the competition assays described herein. In particular, it is contemplated that conservative amino acid changes may be made which do not alter the biological function of the peptide. For instance, one polar amino acid, such as glycine, may be substituted for another polar amino acid; or one acidic amino acid, such as aspartic acid may be substituted for another acidic amino acid, such as glutamic acid; or a basic amino acid, such as lysine, arginine or histidine may be substituted for another basic amino acid; or a non-polar amino acid, such as alanine, leucine or isoleucine may be substituted for another non-polar amino acid.

The degree of homology between the analog amino acid sequence and alboaggreggin native sequence is preferably at least 80%, more preferably at least 90%, most preferably at least 95%.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A method for inhibiting the adhesion of platelets to exposed subendothelial components of blood vessel walls comprising treating the platelets with a polypeptide which binds to the about 45 kDa N-terminal domain of human platelet glycoprotein Ib to inhibit the binding of von Willerbrand factor to said domain, said polypeptide comprising a native polypeptide having an amino acid sequence selected from the group consisting of:
SEQ ID NO:1,
SEQ ID NO:2,
SEQ ID NO:3,
SEQ ID NO:4,
SEQ ID NO:5,
SEQ ID NO:6,
SEQ ID NO:7,
SEQ ID NO:8,
SEQ ID NO:9 and
SEQ ID NO:10, or an analog of said native polypeptide having an amino acid sequence of at least 80% sequence identity with the amino acid sequence of a native polypeptide selected from the above group, wherein one or more amino acids have been changed from the amino acid sequence of said native polypeptide, wherein the change is a conservative amino acid change, which analog retains the property of binding to the about 45 kDa N-terminal domain of human platelet glycoprotein Ib to inhibit the binding of von Willerbrand factor to said domain.

2. A method according to claim 1 wherein the platelets comprise human platelets.

3. A method according to claim 1 wherein the polypeptide has an amino acid sequence of SEQUENCE ID NO:1.

4. A method according to claim 1 wherein the polypeptide has an amino acid sequence of SEQUENCE ID NO:2.

5. A method according to claim 1 wherein the polypeptide has an amino acid sequence of SEQUENCE ID NO:3.

6. A method according to claim 1 wherein the polypeptide has an amino acid sequence of SEQUENCE ID NO:4.

7. A method according to claim 1 wherein the polypeptide has an amino acid sequence of SEQUENCE ID NO:5.

8. A method according to claim 1 wherein the polypeptide has an amino acid sequence of SEQUENCE ID NO:6.

9. A method according to claim 1 wherein the polypeptide has an amino acid sequence of SEQUENCE ID NO:7.

10. A method according to claim 1 wherein the polypeptide has an amino acid sequence of SEQUENCE ID NO:8.

11. A method according to claim 1 wherein the polypeptide has an amino acid sequence of SEQUENCE ID NO:9.

12. A method according to claim 1 wherein the polypeptide has an amino acid sequence of SEQUENCE ID NO:10.

13. A method according to claim 1 wherein the sulfhydryl groups of the polypeptide have been blocked by treatment with a blocking agent to prevent disulfide bond reformation.

14. A method according to claim 1, wherein the sequence identity between the sequence of said polypeptide analog and of said corresponding sequence selected from the group consisting of:
SEQ ID NO:1,
SEQ ID NO:2,
SEQ ID NO:3,
SEQ ID NO:4,
SEQ ID NO:5,
SEQ ID NO:6,
SEQ ID NO:7,
SEQ ID NO:8,
SEQ ID NO:9 and
SEQ ID NO:10,
is 90 percent.

15. A method according to claim 14, wherein said sequence identity is 95 percent.

16. A method for inhibiting adhesion of platelets to exposed subendothelial components of blood vessel walls comprising treating the platelets with a substantially purified platelet-binding protein obtainable from snake venom, said protein comprising two non-identical cysteine-crosslinked polypeptide chains having amino acid sequences of SEQUENCE ID NO:9 and SEQUENCE ID NO:10, respectively, or a single-chain polypeptide subunit thereof, which protein or single-chain polypeptide subunit thereof binds to the about 45 kDa N-terminal domain of human platelet glycoprotein Ib to inhibit binding of von Willebrand factor to said domain without inducing substantial platelet aggregation.

17. A method for inhibiting platelet adhesion to exposed endothelial components of blood vessel walls comprising administering to a mammal in need of such treatment an effective amount of a substantially purified platelet-binding protein obtainable from snake venom, said protein comprising two non-identical cysteine-crosslinked polypeptide chains having amino acid sequences of SEQUENCE ID NO:9 and SEQUENCE ID NO:10, respectively, or a single-chain polypeptide subunit thereof, which protein or a single-chain polypeptide subunit thereof binds to the about 45 kDa N-terminal domain of human platelet glycoprotein Ib to inhibit binding of von Willerbrand factor to said domain without inducing substantial platelet aggregation.

18. A method for inhibiting platelet adhesion to exposed endothelial components of blood vessel walls comprising administering to a mammal in need of such treatment an effective amount of a polypeptide which binds to the about 45 kDa N-terminal domain of human platelet glycoprotein Ib to inhibit the binding of von Willerbrand factor to said domain, said polypeptide comprising a native polypeptide having an amino acid sequence selected from the group consisting of:
SEQ ID NO:1,
SEQ ID NO:2,
SEQ ID NO:3,
SEQ ID NO:4,
SEQ ID NO:5,
SEQ ID NO:6,
SEQ ID NO:7,
SEQ ID NO:8,
SEQ ID NO:9 and
SEQ ID NO:10, or an analog of said native polypeptide having an amino acid sequence of at least 80% sequence identity with the amino acid sequence of a native polypeptide selected from the above group, wherein one or more amino acids have been changed from the amino acid sequence of said native polypeptide, wherein the change is a conservative amino acid change which analog retains the property of binding to the about 45 kDa N-terminal domain of human platelet glycoprotein Ib to inhibit the binding of von Willebrand factor to said domain.

19. A method according to claim 21 wherein the treated mammal is a human being.

20. A method according to claim 18 wherein the polypeptide has an amino acid sequence of SEQUENCE ID NO:1.

21. A method according to claim 18 wherein the polypeptide has an amino acid sequence of SEQUENCE ID NO:2.

22. A method according to claim 18 wherein the polypeptide has an amino acid sequence of SEQUENCE ID NO:3.

23. A method according to claim 18 wherein the polypeptide has an amino acid sequence of SEQUENCE ID NO:4.

24. A method according to claim 18 wherein the polypeptide has an amino acid sequence to SEQUENCE ID NO:5.

25. A method according to claim 18 wherein the polypeptide has an amino acid sequence to SEQUENCE ID NO:6.

26. A method according to claim 18 wherein the polypeptide has an N-terminal amino acid sequence of SEQUENCE ID NO:7.

27. A method according to claim 18 wherein the polypeptide has an amino acid sequence of SEQUENCE ID NO:8.

28. A method according to claim 18 wherein the polypeptide has an amino acid sequence of SEQUENCE ID NO:9.

29. A method according to claim 18 wherein the polypeptide has an amino acid sequence of SEQUENCE ID NO:10.

30. A method according to claim 18 wherein the sulfhydryl groups of the polypeptide have been blocked by treatment with a blocking agent to prevent disulfide bond reformation.

31. A method according to claim 18, wherein the sequence identity between the sequence of said polypeptide analog and of said corresponding sequence selected from the group consisting of:
SEQ ID NO:1,
SEQ ID NO:2,
SEQ ID NO:3,
SEQ ID NO:4,
SEQ ID NO:5,
SEQ ID NO:6,
SEQ ID NO:7,
SEQ ID NO:8,
SEQ ID NO:9 and
SEQ ID NO:10,
is 90 percent.

32. A method according to claim 31, wherein said sequence identity is 95 percent.

* * * * *